US005498499A

United States Patent [19]

Flow et al.

[11] Patent Number: 5,498,499

[45] Date of Patent: * Mar. 12, 1996

[54] PEPTIDES AND ANTIBODIES THAT INHIBIT PLATELET ADHESION

[75] Inventors: Edward F. Flow; Mark H. Ginsberg, both of San Diego; Joseph C. Loftus, Carlsbad, all of Calif.

[73] Assignee: The Scripps Research Institute, La Jolla, Calif.

[*] Notice: The portion of the term of this patent subsequent to Jul. 8, 2007, has been disclaimed.

[21] Appl. No.: 883,669

[22] Filed: May 15, 1992

Related U.S. Application Data

[63] Continuation-in-part of Ser. No. 70,953, Jul. 8, 1987, abandoned, and a continuation of Ser. No. 175,342, Mar. 31, 1988, Pat. No. 5,114,842.

[51] Int. Cl.$^6$ .................... A61K 49/00; A61K 39/00; G01N 33/53
[52] U.S. Cl. .................... 435/7.21; 435/7.1; 435/7.25; 435/7.29; 424/9.1; 424/130.1; 424/139.1; 424/143.1; 424/185.1; 424/1.49; 424/1.53
[58] Field of Search ................... 435/7.1, 70.21, 435/240.27, 7.21, 7.24, 7.25; 424/9, 130.1, 139.1, 143.1, 185.1; 530/388.25, 326, 327

[56] References Cited

U.S. PATENT DOCUMENTS

| 4,421,735 | 12/1983 | Haber et al. | 424/9 |
|---|---|---|---|
| 4,427,646 | 1/1984 | Olexa et al. | 424/1.69 |
| 4,454,106 | 6/1984 | Gansow et al. | 436/506 |
| 4,544,640 | 10/1985 | Soma et al. | 436/506 |
| 5,114,842 | 5/1992 | Plow et al. | 424/1.49 |

OTHER PUBLICATIONS

Shadle, 1983. *Platelet collagen adhesion in a novel assay: identification of a surface adhesion molecule.* U. of Calif., San Diego. Ph.D. Thesis. Cataloged on Dissertation Abstracts Online 44/11B:3280.
Maurer et al, 1980. Proteins and polypeptides as antigens. Meth Enzymol 70:49–70.
Goding, 1983. *Monoclonal Antibodies: Principles and Practice.* Academic Press, Inc., Orlando. p. 11.
Jennings, et al., *Blood* 65: 1112–1119 (1985).
Charo, et al., *PNAS USA* 83: 8351–8355 (1986).
Varon, et al., *PNAS USA* 80: 6992–6995 (1983).
Poncz, et al., *J. Biol. Chem.* 262: 8476–8482 (1987).
Bray, et al., *J. Clin. Invest.* 80: 1812–1817 (1987).
Uzan, et al., *J. Biol. Chem.* 171: 87–93 (1988).
Chard, *An Introduction to Radioimmunoassays and Related Techniques*, Work & Work (eds), pp. 136–141 (1982).
Shadle, et al., *J. Cell Biol.* 99: 2056–60 (1984).
Plow, et al., *PNAS USA* 83: 6002–6006 (1986).
Ginsberg, et al., *J. Clin. Invest.* 78: 1103–1111 (1986) (p. 1104 not provided but added to ref.).
Jemmerson, et al., *Science* 232: 1001–1004 (1986).
Miles, et al., *Nature* 219: 186–9 (1968).
Wisdom, *Clin. Chem.* 22: 1243–1255 (1976).
Ginsberg, et al., *Chem. Abst.* 106 (25): 210580x (1986).
Matsueda, et al., *Chem. Abst.* 108 (15): 128120e (1987).
Shani, et al., *Nucl. Med. Biol.* 13: 379–382 (1986).
Hynes, *Cell* 48: 549–554 (1987).
Haber, in *Monoclonal Antibodies and New Trends in Immunoassays*, Bizollon (ed.), pp. 81–90, Elsevier Publishers (1984).
Bennett, et al., *PNAS USA* 80: 2417–2421 (1983).
Kohler, et al., *Nature* 256: 495–7 (1975).
Galfre, et al., *Meth. Enzymol.* 73: 3–46 (1981).
Lewis, et al., *Biochemistry* 22: 948–54 (1983).
Wakabayashi, et al., *J. Biol. Chem.* 261: 11097–11105 (1986).
Frelinger, et al., *J. Biol. Chem.* 265: 6346–6352 (1990).
Frelinger, et al., *Circulation* 78; 1231 (Abstract; 1988).
Frelinger, et al., *Clin. Res.* 35(3): 598A (Abstract; 1987).
Lam, et al., *J. Biol. Chem.* 262: 947–50 (1987).
Pytela, et al., *Science* 231: 1559–62 (1986).
Nilsson, et al., *Molecular Immunol.* 24: 487–94 (1987).

*Primary Examiner*—Toni R. Scheiner
*Assistant Examiner*—James Grun
*Attorney, Agent, or Firm*—April C. Logan

[57] ABSTRACT

A polypeptide analog capable of immunologically mimicking a linear hGPIIb antigenic determinant expressed when platelet-associated GPIIb-IIIa binds fibrinogen is disclosed. An antibody that immunoreacts with the polypeptide and hGPIIb when hGPIIb is present as a platelet-associated GPIIb-IIIa/fibrinogen complex is also disclosed. Further disclosed are diagnostic systems and methods for assaying fibrinogen-bound platelets in a vascular fluid sample using the polypeptides and/or antibodies of the invention.

4 Claims, 5 Drawing Sheets

```
  1  CGAGAATATGACCTTGGTCAGGTGCAGTGGCTCACGCCTGTAATCCCAGTACTTTGGGAG   60
     R  E  Y  D  L  G  Q  V  Q  W  L  T  P  V  I  P  V  L |W  E

61  GCCAAGGCAGGCAGATCACCTGAGGTCAGGAGTTCGAGGTCAGCCTTGCCGAACCCCTTT  120
     A  K  A  G  R  S  P  E  V  R  S  S  R  S| A  L  P  N  P  F

121  CCAGCCTCCCTGGTGGTGGCAGCAGAAGAAGGTGAGAGGGAGCAGAACAGCTTGGACAGC  180
     P  A  S  L  V  V  A  A  E  E  G  E |R  E  Q  N  S  L  D  S

181  TGGGGACCCAAAGTGGAGCACACCTATGAGCTCCACAACACTGGCCCTGGGACTGTGAAT  240
     W  G  P  K  V |E  H  T  Y  E  L  H  N  T  G  P  G  T  V  N

241  GGTCTTCACCTCAGCATCCACCTTCCGGGACAGTCCCAGCCCTCCGACCTGCTCTACATC  300
     G  L  H  L  S  I  H  L  P  G  Q  S  Q  P  S  D  L  L  Y  I

301  CTGGATATACAGCCCCAGGGGGCGCTTCAGTGCTTCCCACAGCCTCCTGTCAATCCTCTC  360
     L  D  I  Q  P  Q  G  A  L  Q  C  F  P  Q  P  P  V  N  P  L

361  AAGGTGGACTGGGGGCTGCCCATCCCCAGCCCCTCCCCATTCACCCGGCCCATCACAAG   420
     K  V  D  W  G  L  P  I |P  S  P  S  P  I  H  P  A  H  H  K

421  CGGGATCGCAGACAGATCTTCCTGCCAGAGCCCGAGCAGCCCTCGAGGCTTCAGGATCCA  480
     R  D  R |R  Q| I  F  L  P  E  P  E  Q  P  S  R▲L  Q  D  P

481  GTTCTCGTAAGCTGCGACTCGGCGCCCTGTACTGTGGTGCAGTGTGACCTGCAGGAGATG  540
     V  L  V  S  C  D  S  A  P  C  T  V  V  Q  C  D  L  Q  E  M

541  GCGCGCGGGCAGCGGGCCATGGTCACGGTGCTGGCCTTCCTGTGGCTGCCCAGCCTCTAC  600
     A  R  G  Q  R  A  M  V  T  V  L  A  F  L  W  L  P  S  L  Y

601  CAGAGGCCTCTGGATCAGTTTGTGCTGCAGTCGCACGCATGGTTCAACGTGTCGTTTGAG  660
     Q  R  P  L  D  Q  F  V  L  Q  S  H  A  W  F  N  V  S  F  E

661  GAAGAAGCAAAGTGTAGTAGTTAGAATGGTGATTTCTGAGCAAGAAGATGGGGGCTCTGT  720
     E  E  A  K  C  S  S  *

721  ATTCCTGGCCAAGTAGCTTGGCTTCTCTGGGTCTCAGTTTGCTGCCAAAGCAAACGAGGA  780

781  TAATACTGATCCTACCTGTAATAGGACCATTGAAAGGATTTCACAGGATGAGGTTTATGA  840

841  AAATACTTTATAGTTAATAATTCTACATCATATACCTGAAATTTGCTAAGAGAGAAAAAT  900

901  CTTAAAACGTTCTCACCACAAAAGATAACTATGTGAGGTGATACATACGCTAATTAGCTT  960

961  GATTGTGGTAATCCTTTCACAATGTATACATATACCAAAACATCATATTGCACACTGTGA  1020

1021 ATATATACAATTTATTTGTCAATTATACCTCAATACAGCTGGAAATACATAAATTTTCAT  1080

1081 GCACTGTGTAAATATGAGAGATGG  1104
```

FIG. 1

PEPTIDES AND ANTIBODIES THAT INHIBIT PLATELET ADHESION

This invention was made with government support under National Institutes of Health Contracts HL-16411 and HL-28235. The government has certain rights in the invention.

CROSS REFERENCE TO RELATED APPLICATIONS

This application is a continuation-in-part of U.S. Ser. No. 070,953, filed Jul. 8, 1987, now abandoned and a continuation of U.S. Ser. No. 175,342, filed Mar. 31, 1988, now U.S. Pat. No. 5,114,842 the disclosures of which are hereby incorporated by reference.

TECHNICAL FIELD

The present invention relates to DNA and recombinant DNA molecules that include a DNA sequence encoding a structural gene for that portion of the GPIIb heavy chain (hGPIIb) that forms an antigenic determinant when platelet-associated GPIIb-GPIIIa binds fibrinogen. The present invention also relates to hGPIIb cryptic determinant polypeptide analogs and antibodies that immunoreact with the polypeptide analogs.

BACKGROUND

Cell adhesion generally involves recognition of specific adhesive proteins by cell surface receptors. A family of cell surface receptors of particular interest to the present invention are the integrins.

According to Hynes, Cell 48:549–554 (1987), integrins are a functionally and structurally related group of receptors that interact with a wide variety of ligands including extracellular matrix glycoproteins, complement and other cells. Integrins participate in cell-matrix and cell-cell adhesion in many physiologically important processes including embryological development, hemostasis, thrombosis, wound healing, immune and nonimmune defense mechanisms and oncogenic transformation. Two human genetic diseases, Glazmann's thrombasthenia and leukocyte adhesion deficiency, involve members of the integrin family.

Structurally, integrins are heterodimeric complexes comprised of noncovalently associated alpha and beta subunits. Within the integrin family there are recognized groups related by the presence of a similar beta subunit and members within each group are distinguished by unique alpha subunits.

For instance, GPIIb-IIIa is a noncovalent, $Ca^{++}$ dependent, heterodimer complex comprised of alpha and beta subunits. Jennings et al., *J. Biol. Chem.*, 257:10458–10466 (1982). The alpha subunit, GPIIb consists of a heavy chain (hGPIIb) having a relative molecular weight of about 120 kilodaltons (KDa), and a light chain (lGPIIb) of about 20 KDa that are linked together by disulfide bonds. The beta subunit, GPIIIa is a single chain polypeptide of about 100 KDa. Phillips et al., *J. Biol. Chem.*, 252:2121–2126 (1977). Cell surface molecules immunologically related to GPIIb-IIIa have been identified on a variety of cell types. See Thiagarajan et al., *J. Clin. Invest.*, 75:896–901 (1985); Plow et al., *PNAS USA*, 83:6002–6006 (1986); and Fitzgerald et al., *J. Biol. Chem.*, 260:10893–10896 (1985).

GPIIb-IIIa contributes to platelet function through interactions with RGD-containing proteins such as fibrinogen [Bennett et al., *PNAS USA*, 80:2417–2421 (1983)], fibronectin [Ginsberg et al., *J. Clin. Invest.*, 71:619–624 (1983)], and von Willebrand factor [Ruggeri et al., *PNAS USA*, 79:6038–6041 (1982)], and therefore is a component of the common platelet adhesive protein receptor [Pytela et al., *Science*, 231:1559–1562 (1986) and Plow et al., *J. Biol. Chem.*, 259:5388–5391 (1984)].

Recent evidence indicates that GPIIb-IIIa is one of several adhesion receptors that share a similar beta subunit and the functional property of recognizing the tripeptide amino acid residue sequence Arg-Gly-Asp (using single letter symbols, RGD). Pytela et al., *Science*, 231:1559–1562 (1986) and Ruoslahti et al., *Cell*, 44:517–518 (1986). In addition to GPIIb-IIIa, this group of related receptors includes the vitronectin receptor (VnR) and fibronectin receptor (FnR) isolated from osteosarcoma cells [Pytela et al., *Cell*, 40:191–198 (1985), Pytela et al., *PNAS USA*, 82:5766–5770 (1985) and Sanchez-Madrid et al., *J. Exp. Med.*, 158:1785–1803 (1983)].

The similar functional, structural, and antigenic properties of these proteins suggests GPIIb-IIIa and VnR (a GPIIIa-containing receptor) are members of an adhesion receptor group for which the designation "cytoadhesin" has been proposed. Plow et al., *PNAS USA*, 83:6002–6006 (1986). Within the cytoadhesin group, distinct alpha subunits combine with a common or very similar beta subunit, resulting in functionally distinguishable receptors. Ginsberg et al., *J. Biol. Chem.*, 262:5437–5440 (1987).

At least two other groups of heterodimeric adhesion receptors have been identified in which a common beta subunit combines with a number of distinct alpha subunits. One group is found on leukocytes and has been referred to as the leukocyte adhesion family and includes LFA-1, Mac-1, and p150,95. Sanchez-Madrid et al., *J. Exp. Med.*, 158:1785–1803 (1983) and Springer et al., *Ciba. Found. Symp.*, 118:102–126 (1986). The other is more widely distributed and has been referred to as the VLA family Hemler et al., *J. Biol. Chem.*, 262:3300–3309 (1987). The beta subunit of the VLA family [Hemler et al., *J. Biol. Chem.*, 262:3300–3309 (1987)] in the chicken has been cloned and sequenced and designated "Integrin" [Tamkun et al., *Cell*, 46:271–282 (1986)]. The sequence of chicken integrin is similar to that of GPIIIa [Fitzgerald et al., *J. Biol. Chem.*, 262:3936–3939 (1987)] and to the beta subunit of the leukocyte adhesion family [Kishimoto et al., *Cell*, 48:681–690 (1987)]. Moreover, partial sequences of several alpha subunits also indicate similarities. Ginsberg et al., *J. Biol. Chem.*, 262:5437–5440 (1987); Suzuki et al., *PNAS USA*, 83:8614–8618 (1986); and Charo et al., *PNAS USA*, 83:8351–8356 (1986).

The sites on GPIIb-IIIa, or the other cytoadhesins, that are required for their functions as adhesion receptors are not well characterized. Several observations suggest that a functionally significant site on GPIIb-IIIa is near the epitope defined by the monoclonal antibody PMI-1. This antibody binds to the heavy chain of GPIIb [Shadle et al., *J. Cell. Biol.*, 99:2056–2060 (1984)] and defines a region of GPIIb that is associated with several distinct functional activities. First, PMI-1 inhibits adhesion of washed platelets to collagen. Shadle et al., *J. Cell. Biol.*, 99:2056–2060 (1984). Second, the surface orientation of this region is regulated by divalent cations because millimolar (mM) concentrations of calcium or magnesium suppress expression of the PMI-1 epitope. Ginsberg et al., *J. Clin. Invest.*, 78:1103–1111 (1986). Third, abnormal divalent cation regulation of the conformation of this site is associated with a functional thrombasthenic state. Ginsberg et al., *J. Clin. Invest.*, 78:1103–1111 (1986). Fourth, stimulation of platelets with up to 100 micromolar adenosine diphosphate (ADP) or epinephrine, 1 unit per milliliter thrombin, or 50 micrograms per milliliter calf skin collagen does not substantially increase the binding of PMI-1 antibodies to platelets.

BRIEF SUMMARY OF THE INVENTION

It has now been found that cell surface receptors that have specifically bound a ligand can be distinguished from non-occupied receptors by the presence of a ligand-induced antibody binding site (LIBS). That is, a class of antigenic determinants has been discovered that are expressed when a cell surface receptor specifically binds a ligand but are not expressed by either the non-occupied receptor or the non-bound ligand. Therefore, in one embodiment, the present invention contemplates a method of forming a monoclonal antibody that immunoreacts with a ligand-induced binding site expressed by a receptor-ligand complex wherein the complex contains a cell surface receptor and a ligand that are specifically bound, which method comprises:

(a) immunizing a mammal with the complex;

(b) removing antibody-producing cells from the immunized mammal and preparing a suspension of the cells;

(c) treating the cells with a transforming agent to produce transformed antibody-producing cells;

(d) cloning, by limiting dilution in a tissue culture medium that will not sustain non-transformed cells, the cells treated in step (c) to produce cloned transformants;

(e) evaluating the tissue culture medium of the cloned transformants for the presence of secreted antibody molecules that immunoreact with the receptor-ligand complex but do not immunoreact with the cell surface receptor or the ligand when either is in non-bound form;

(f) selecting and growing in a tissue culture medium a cloned transformant producing the secreted antibody molecules; and (g) harvesting the secreted antibody molecules from the culture medium of the selected and cloned transformant.

In another embodiment, the present invention contemplates a method of forming a monoclonal antibody that immunoreacts with a ligand-induced binding site expressed by a receptor-ligand complex wherein the complex contains a cell surface receptor and a ligand that are specifically bound, which method comprises:

(a) immunizing a mouse with the complex;

(b) removing the spleen from the mouse and preparing a suspension of the spleen cells;

(c) fusing the spleen cells with mouse myeloma cells in the presence of a fusion promoter to produce antibody-secreting hybridomas;

(d) diluting and culturing the fused cells in separate wells in a medium that will not support the unfused myeloma cells;

(e) evaluating the supernatant in each well containing a hybridoma for the presence of secreted antibody molecules that immunoreact with the receptor-ligand complex but do not immunoreact with the cell surface receptor or the ligand when either is in non-bound form;

(f) selecting and cloning a hybridoma secreting the antibody molecules; and (g) harvesting the antibody molecules from the supernatant of the hybridoma, above the clones.

Further contemplated is a method of forming a monoclonal antibody that immunoreacts with a ligand-induced binding site expressed by a receptor-ligand complex wherein the complex contains a cell surface receptor and a ligand that are specifically bound, which method comprises:

(a) immunizing a mouse with the complex;

(b) removing the spleen from the mouse and making a suspension of the spleen cells;

(c) fusing the spleen cells with mouse myeloma cells in the presence of a fusion promoter to produce antibody-secreting hybridomas;

(d) diluting and culturing the fused cells in separate wells in a medium that will not support the unfused myeloma cells;

(e) evaluating the supernatant in each well containing a hybridoma for the presence of secreted antibody molecules that immunoreact with the cell surface receptor-ligand complex but do not immunoreact with the cell surface receptor or the ligand when either is in non-bound form;

(f) selecting and cloning a hybridoma secreting the antibody molecules;

(g) transferring the clones intraperitoneally into a mouse; and (h) harvesting the ascites or serum from the mouse, which ascites or serum contains the desired antibody.

Also contemplated is a method of detecting in vivo the presence of a receptor-ligand complex wherein the complex contains a cell surface receptor and a ligand that are specifically bound, which comprises the steps of:

(a) intravenously administering to a human subject an effective amount of a monoclonal antibody composition comprising a physiologically tolerable diluent and antibody molecules that immunoreact with the receptor-ligand complex but do not immunoreact with the cell surface receptor or the ligand when either is in non-bound form, the antibody molecules being linked to an in vivo indicating means;

(b) maintaining the administered subject for a predetermined time period sufficient for the antibody molecules to immunoreact with the receptor-ligand complex in vivo and form an immunoreaction product; and (c) assaying for the presence of any immunoreaction product formed in step (b) and thereby the presence of the complex in the subject.

Still further contemplated is a method of assaying for the presence of a receptor-ligand complex in a vascular fluid sample wherein the complex contains a cell surface receptor and a ligand that are specifically bound, which method comprises the steps of:

(a) forming an immunoreaction admixture by admixing the vascular fluid sample with a monoclonal antibody composition containing antibody molecules that immunoreact with the receptor-ligand complex but do not immunoreact with the cell surface receptor or the ligand when either is in non-bound form;

(b) maintaining the admixture for a time period sufficient for the antibody molecules to immunoreact with any receptor-ligand complex present in the sample and form an immunoreaction product; and (c) detecting the presence of any immunoreaction product formed in step (b) and thereby the presence of the complex in the sample.

In another embodiment, the present invention contemplates a method of assaying a platelet-containing vascular fluid sample for the presence of platelets expressing a GPIIb-IIIa-ligand complex, which method comprises the steps of:

(a) forming an immunoreaction admixture by admixing the vascular fluid sample with an effective amount of a monoclonal antibody composition containing anti-GPIIb-IIIa antibody molecules produced by hybridoma PMI-1 or PMI-2;

(b) maintaining the admixture for a time period sufficient for the antibodies to immunoreact with any fibrinogen-bound platelets present in the sample and form an immunoreaction product; and (c) detecting the presence of any immunoreaction product formed in step b.

Also contemplated is a method of detecting the presence of a thrombus in vivo comprising the steps of:

(a) intravenously administering to a human subject an effective amount of a monoclonal antibody composition comprising a physiologically tolerable diluent and anti-GPIIb-IIIa antibody molecules linked to an in vivo indicating means, the antibody molecules being those produced by hybridoma PMI-1 or PMI-2;

(b) maintaining the administered subject for a predetermined time period sufficient for the antibody molecules to immunoreact with fibrinogen-bound platelets in vivo and form an immunoreaction product; and (c) assaying for the presence of any immunoreaction product formed in step b.

A diagnostic system in kit form for assaying for the presence of a receptor-ligand complex in a vascular fluid sample, said complex containing a cell surface receptor and a ligand that are specifically bound, which system comprises:

(a) a package containing, in an amount sufficient to perform at least one assay, a monoclonal antibody composition containing antibody molecules that immunoreact with said receptor-ligand complex but do not immunoreact with the cell surface receptor or the ligand when either is in non-bound form.

A diagnostic system in kit form for assaying for the presence of cell receptor-ligand complex in vivo, said complex containing a cell surface receptor and a ligand that are specifically bound, which system comprises:

(a) a package containing, in an amount sufficient to perform at least one assay, a monoclonal antibody composition containing antibody molecules that immunoreact with said receptor-ligand complex but do not immunoreact with the cell surface receptor or the ligand when either is in non-bound form, said antibody molecules linked to an in vivo indicating means.

A diagnostic system in kit form for assaying a vascular fluid sample for the presence of platelets expressing a GPIIb-IIIa-ligand complex, which system comprises:

(a) a package containing anti-GPIIb-IIIa, in an amount sufficient to perform at least one assay, anti-GPIIb-IIIa antibody molecules produced by hybridoma PMI-1 or PMI-2.

A diagnostic system in kit form for assaying for the presence of a thrombus in vivo comprising:

(a) a package containing, in an amount sufficient to perform at least one assay, a monoclonal antibody composition containing anti GPIIb-IIIa antibody molecules produced by hybridoma PMI-1 or PMI-2, said antibody molecules linked to an in vivo indicating means.

Furthermore, it has now been discovered that platelet GPIIb-IIIa-ligand complexes express two cryptic antigenic determinant type LIBS recognized by antibody molecules produced by hybridomas PMI-1 and PMI-2. In addition, a polypeptide capable of mimicking the cryptic determinant recognized by monoclonal antibody PMI-1 has been deduced from the DNA sequence that encodes the portion of the GPIIb protein that forms the cryptic determinant in vivo.

Thus, the present invention contemplates a DNA segment comprising no more than about 12,000 nucleotide base pairs including a sequence defining a structural gene coding for a portion of the GPIIb protein having an amino acid residue sequence as shown in FIG. 1 from about residue 50 to about residue 140.

In another embodiment, a recombinant DNA molecule comprising a vector operatively linked to a DNA segment that defines a structural gene coding for a portion of the GPIIb protein having an amino acid residue sequence as shown in FIG. 1 from about residue 50 to about residue 145 is also contemplated.

Further contemplated is a hGPIIb cryptic determinant polypeptide analog comprising no more than about 50 amino acid residues and including an amino acid residue sequence represented by the formula:

−PSPSPIHPAHHKRDRRQ−.

Also contemplated are hybridomas designated PMI-1 and PMI-2, that produce antibody molecules that immunoreact with fibrinogen-bound platelets.

A monoclonal antibody composition comprising antibody molecules produced by hybridoma PMI-1 that immunoreact with fibrinogen-bound platelets is contemplated.

BRIEF DESCRIPTION OF THE DRAWINGS

FIG. 1 illustrates the nucleotide sequence and a corresponding amino acid residue sequence of a cDNA that codes for a portion of the precursor protein of GPIIb wherein the nucleotide sequence is shown from left to right and in the direction of 5' terminus to 3' terminus using the single letter nucleotide base code represented as an uninterrupted linear series of bases from base 1 to base 1104. The amino acid residue sequence is shown from left to right and in the direction from amino-terminus to carboxy-terminus using the single letter amino acid residue code represented as an uninterrupted linear series of residues from residue 1 (R) at the amino-terminus to residue 227 (S) at the carboxy-terminus.

The reading frame is indicated by the placement of the deduced amino acid residue sequence below the nucleotide sequence such that the single letter that represents each amino acid residue is located below the first base in the corresponding codon.

The locations within the GPIIb precursor protein of amino acid residue sequences corresponding to polypeptide designated p129–145 and the polypeptide designated p114–156 are shown in the large and small boxes, respectively. The locations of polypeptides designated p19–34 and p53–65 are shown by the double or single line underlining, respectively. The amino acid residue sequence of a proposed amino-terminus for the light chain of GPIIb is shown by the dotted line, and the arrow marks the potential site of cleavage for generating the heavy and light chains of GPIIb.

Figure 2:
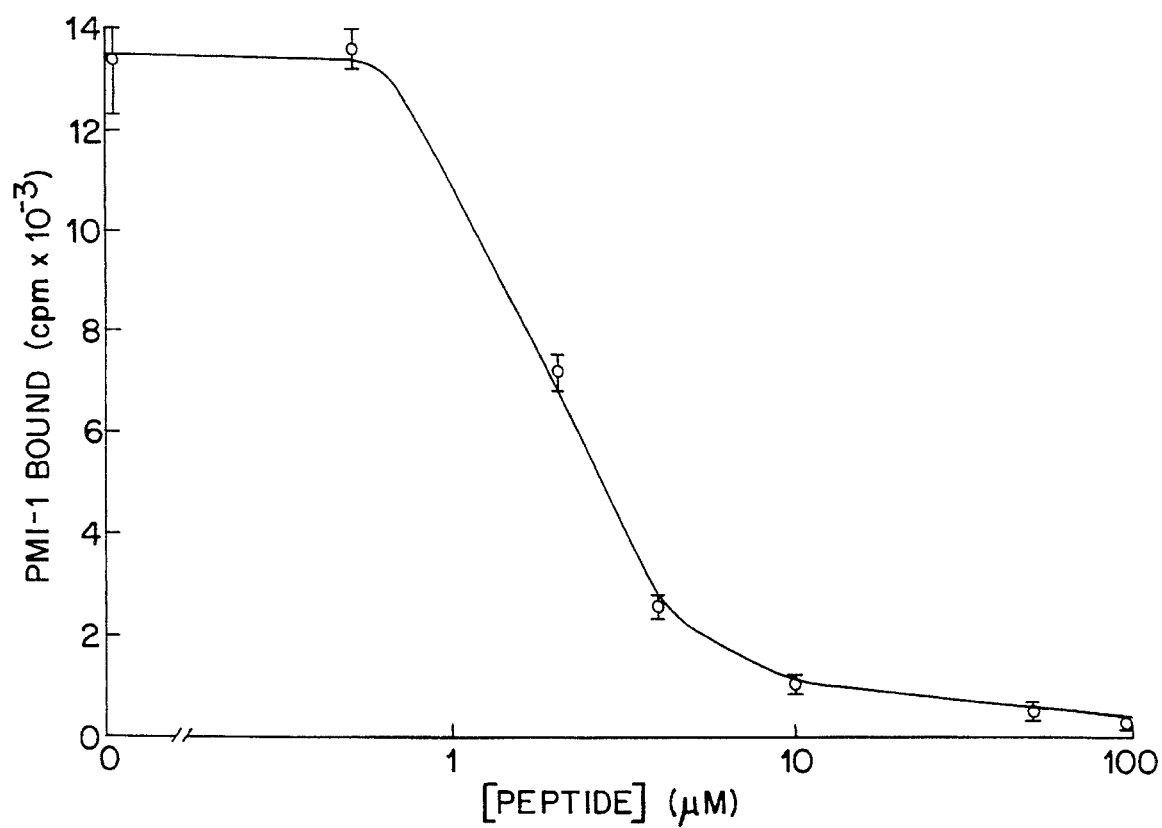

FIG. 2 is a graph illustrating the effect of polypeptide p129–145 on antibody PMI-1 binding to platelets. Platelets were admixed with EDTA to a concentration of 5 mM to allow full exposure of the PMI-1 epitope on hGPIIb. Thereafter the platelets were admixed with various concentrations of polypeptide p129–149 ranging from 0 to 100 micromolar (μM) and with the $^{125}$I-labeled PMI-1 antibody as described in Example 9. Percentage of $^{125}$I-labeled PMI-1 bound to platelets was plotted against the concentration of polypeptide added to the assay.

Figure 3:
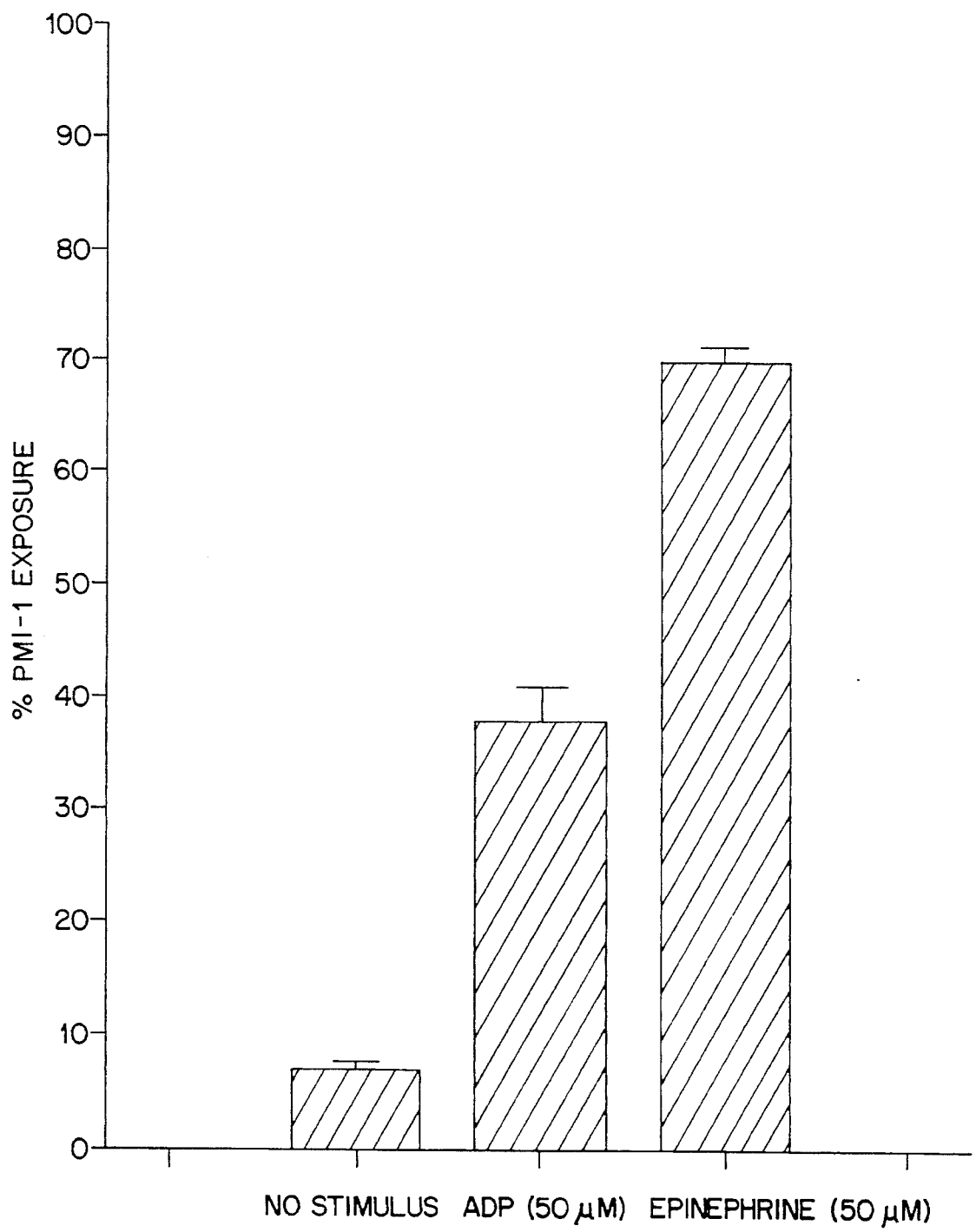

FIG. 3 illustrates exposure of the PMI-1 epitope on stimulated, fibrinogen-bound platelets determined as described in Example 10. The amount of $^{125}$I-labeled PMI-1 that immunoreacts with fibrinogen-bound platelets under conditions of (1) no stimulus, (2) stimulation with 50 μM ADP, or (3) stimulation with 50 μM epinephrine was determined and expressed as a percent relative to the amount of $^{125}$I-PMI-1 immunologically bound to non-stimulated platelets in the presence of 5 mM EDTA.

Figure 4B:
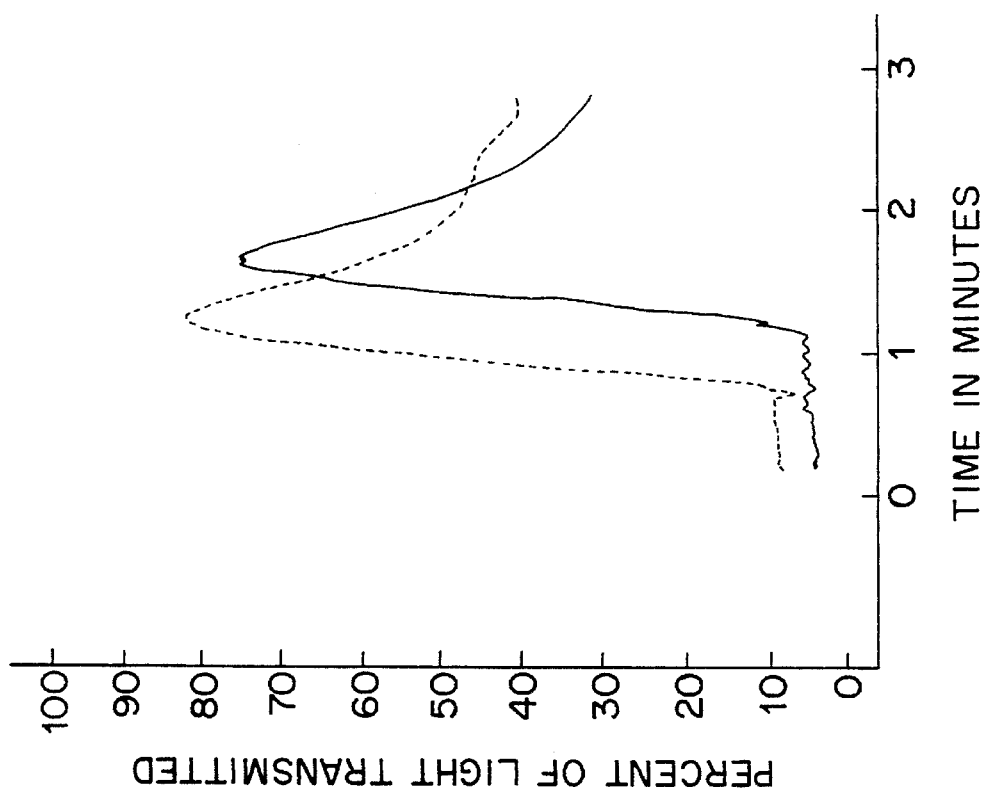
Figure 4A:
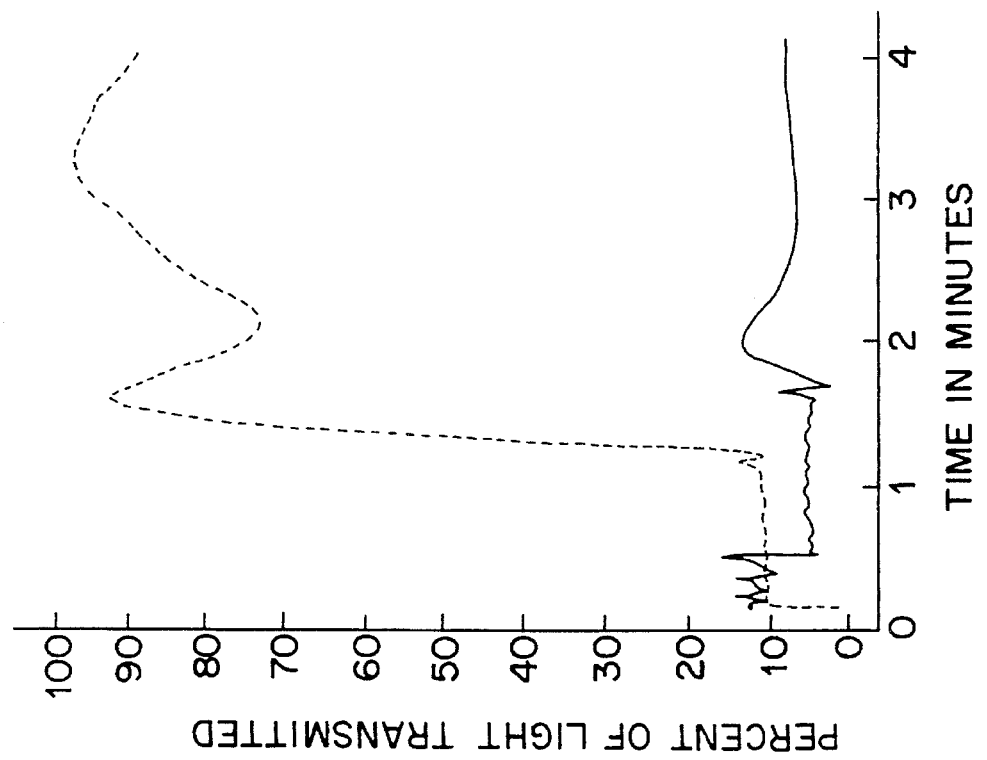

FIGS. 4A and 4B are recorder tracings that illustrate the effect of polypeptides p129–145 and p144–156 on platelet aggregation as described in Example 11. A linear plot is shown of the percent of light transmitted versus time in minutes, where 100 percent transmittance indicates maximum platelet aggregation. FIG. 4A depicts percent light transmitted by a control solution of platelet-rich plasma (PRP) in Tyrode's buffer (broken line) and by PRP that further contains 1 mM polypeptide p129–145 (solid line). FIG. 4B depicts the percent light transmitted by the control solution (broken line) and by PRP further containing 1 mM polypeptide p144–156 (solid line).

Figure 5:
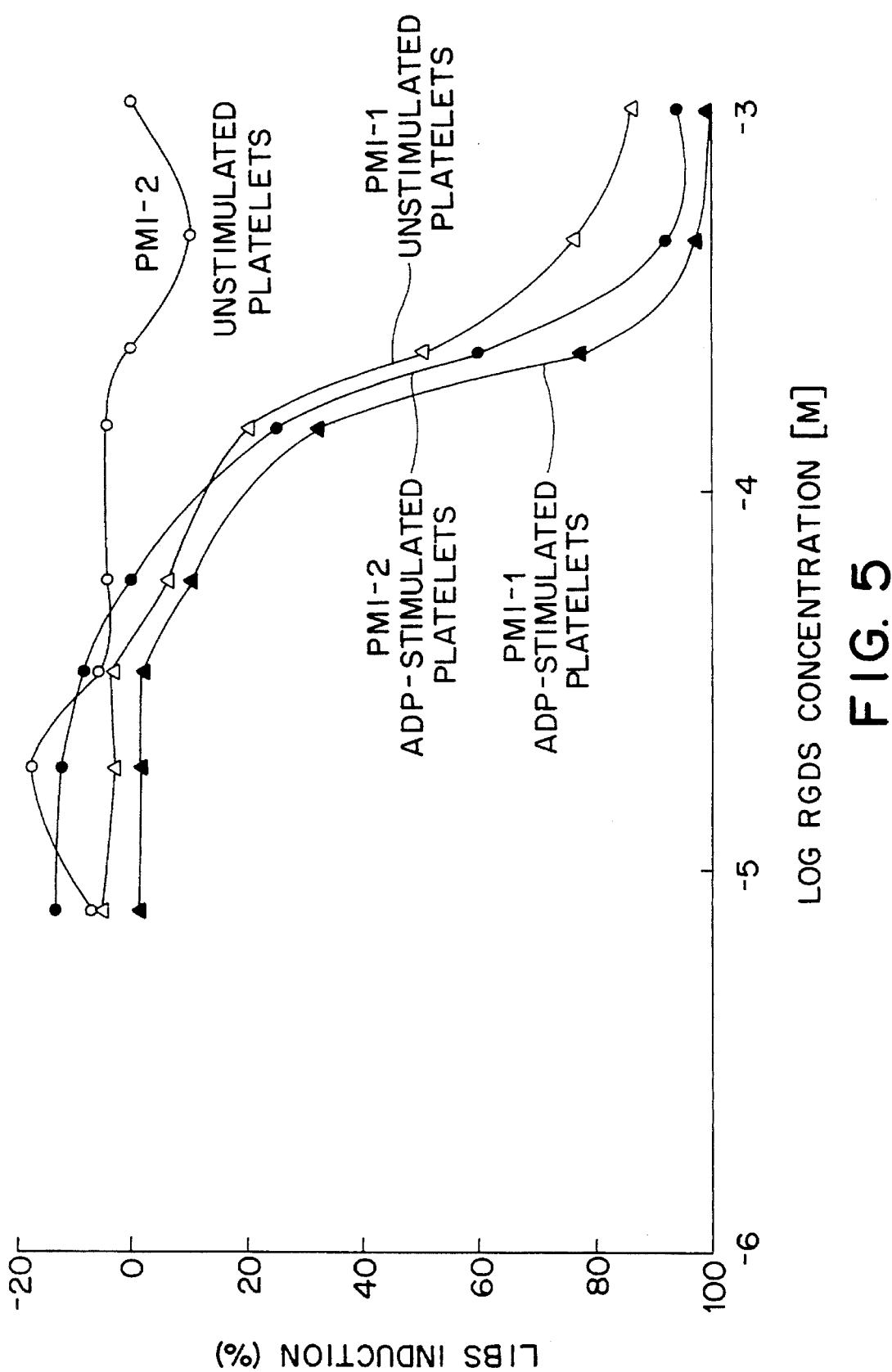

FIG. 5 is a graph illustrating the expression of two distinct ligand induced binding sites by platelet GPIIb-IIIa. Each LIBS was induced by the specific binding of a ligand, in the form of a polypeptide having the amino acid residue sequence RGDS, to form a GPIIb-IIIa ligand (GPIIb-polypeptide) complex. The percentage of LIBS expression by various polypeptide concentrations was determined as described in Example 13A.

DETAILED DESCRIPTION OF THE INVENTION

A. Definitions

Amino Acid: All amino acid residues identified herein are in the natural L-configuration. In keeping with standard polypeptide nomenclature, *J. Biol. Chem.* 243: 3557–59, (1969), abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carboxy-terminus. Furthermore, it should be noted that a dash at the beginning or end of an amino acid residue sequence indicates a bond to a further sequence of one or more amino acid residues up to a total of about fifty residues in the polypeptide chain.

Polypeptide and Peptide: Polypeptide and peptide are terms used interchangeably herein to designate a linear series of no more than about 50 amino acid residues connected one to the other by peptide bonds between the alpha-amino and carboxy groups of adjacent residues.

Protein: Protein is a term used herein to designate a linear series of greater than 50 amino acid residues connected one to the other as in a polypeptide.

Nucleoside and Nucleotide: A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide.

Base Pair (bp): A hydrogen-bonded partnership of adenine (A) with thymine (T), or of cytosine (C) with guanine (G) in a double stranded DNA molecule.

Receptor: Receptor and receptor protein are terms used herein to indicate a biologically active proteinaceous molecule that specifically binds to (or with) other molecules.

Ligand and Cognate Ligand: Ligand refers to a molecule that contains a structural portion that is bound by specific interaction with a particular receptor protein.

Ligand Induced Binding Site (LIBS): A LIBS is a neo-antigenic determinant that is expressed by a cell surface receptor-ligand complex but is not expressed by either the non-occupied receptor or the non-bound ligand. A LIBS can be either "conformational" or "sequential". A LIBS can be the result of specific alterations of the receptor induced by ligand binding, i.e., a "cryptic antigenic determinant" or it can be formed by a combination of receptor and ligand amino acid residues at a receptor-ligand contact site.

Cryptic Antigenic Determinant: Refers to a neo-antigenic determinant formed by changes in conformation or membrane-surface orientation of a receptor protein upon binding to its cognate (specific) ligand. The receptor proteins described herein do not normally express a cryptic antigenic determinant unless the receptor has specifically bound a ligand.

B. DNA Segments

In living organisms, the amino acid residue sequence of a protein or polypeptide is directly related via the genetic code to the deoxyribonucleic acid (DNA) sequence of the structural gene that codes for the protein. Thus, a structural gene can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences can code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

A DNA segment of the present invention includes a structural gene that encodes a protein containing a GPIIb-related amino acid residue sequence, i.e., a GPIIb-related protein. A GPIIb-related amino acid residue sequence is a sequence of at least about 10 residues whose sequence is homologous, preferably identical, to a portion of the amino acid residue sequence shown in FIG. 1 from about residue 50 to about residue 227.

A DNA segment of the present invention includes a DNA sequence that encodes an amino acid residue sequence as shown in FIG. 1 from about residue 50 to about residue 145. In another embodiment, a DNA segment that includes a DNA sequence that encodes an amino acid residue sequence as shown in FIG. 1 from about residue 50 to about residue 227 is contemplated. Also contemplated is a DNA segment that includes a DNA sequence encoding an amino acid residue sequence as shown in FIG. 1 from about residue 146 to about residue 227. Preferably a DNA segment of this invention encodes an amino acid residue sequence as shown in FIG. 1 from about residue 1 to about residue 227. Preferably, the DNA sequence is present as an uninterrupted linear series of codons where each codon codes for an amino acid residue found in the above described amino acid residue sequences, i.e., a DNA sequence containing no introns.

Thus, a DNA segment consisting essentially of the nucleotide sequence shown in FIG. 1 from about base 148 to about base 435 constitutes one embodiment of the present invention. A DNA segment consisting essentially of the nucleotide sequence shown in FIG. 1 from about base 148 to about base 681 constitutes another embodiment of the invention. Preferably, a DNA segment of the present invention consists essentially of the nucleotide sequence shown in FIG. 1 from about base 1 to about base 1104.

A DNA segment of the present invention that encodes a GPIIb-related amino acid residue sequence can easily be synthesized by chemical techniques, for example, the phosphotriester method of Matteucci et al., *J. Am. Chem. Soc.*, 103:3185 (1981). Of course, by chemically synthesizing the coding sequence, any desired modifications can be made simply by substituting the appropriate bases for those encoding the native amino acid residue sequence. However, DNA molecules including sequences exactly homologous to those shown in FIG. 1 are preferred.

Furthermore, DNA segments consisting essentially of structural genes encoding the GPIIb-related proteins can be obtained from recombinant DNA molecules containing those genes. For instance, the plasmid type recombinant DNA molecule HEL-41 contains the DNA sequence shown in FIG. 1 and thus encodes the amino acid residue sequence shown in FIG. 1 from residue 1 to residue 227. A culture of *Escherichia coli* (E. coli) transformed with HEL-41 has been deposited pursuant to Budapest Treaty requirements with the American Type Culture Collection, (ATCC) 12301 Parklawn Drive, Rockville, Md. 20852 on Jul. 7, 1987 and was assigned accession number 67456.

A DNA segment that includes a DNA sequence encoding a GPIIb-related amino acid residue sequence can be prepared by operatively linking (ligating) appropriate restriction fragments from the above deposited plasmid using well known methods. The DNA molecules of the present invention produced in this manner typically have cohesive termini, i.e., "overhanging" single-stranded portions that extend beyond the double-stranded portion of the molecule. The presence of cohesive termini on the DNA molecules of the present invention is preferred.

Also contemplated by the present invention are ribonucleic acid (RNA) equivalents of the above described DNA segments.

C. Recombinant DNA Molecules

A recombinant DNA molecule of the present invention can be produced by operatively linking a vector to a DNA segment of the present invention.

As used herein, the term "vector" refers to a DNA molecule capable of autonomous replication in a cell and to which another DNA segment can be operatively linked so as to bring about replication of the attached segment. Vectors capable of directing the expression of genes encoding proteins having GPIIb-related amino acid residue sequences are referred to herein as "expression vectors". Thus, a recombinant DNA molecule (rDNA) is a hybrid DNA molecule comprising at least two nucleotide sequences not normally found together in nature.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector contemplated by the present invention is at least capable of directing the replication, and preferably also expression, of the gene encoding a protein having a GPIIb-related amino acid residue sequence included in DNA segments to which it is operatively linked.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the gene encoding a GPIIb-related amino acid residue sequence in a bacterial host cell, such as *E. coli*, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Bio-Rad Laboratories, (Richmond, Calif.) and pPL and pKK223 available from Pharmacia, Piscataway, N.J.

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), and pTDT1 (ATCC, #31255).

In preferred embodiments, the eucaryotic cell expression vectors used to construct the recombinant DNA molecules of the present invention include a selection marker that is effective in a eucaryotic cell, preferably a drug resistance selection marker. A preferred drug resistance marker is the gene whose expression results in neomycin resistance, i.e., the neomycin phosphotransferase (neo) gene. Southern et al., *J. Mol. Appl. Genet.*, 1:327–341 (1982).

The use of retroviral expression vectors to form the rDNAs of the present invention is also contemplated. As used herein, the term "retroviral expression vector" refers to a DNA molecule that includes a promoter sequence derived from the long terminal repeat (LTR) region of a retrovirus genome.

In preferred embodiments, the expression vector is typically a retroviral expression vector that is preferably replication-incompetent in eucaryotic cells. The construction and use of retroviral vectors has been described by Sorge et al., *Mol. Cell. Biol.*, 4:1730–37 (1984).

A variety of methods have been developed to operatively link DNA to vectors via complementary cohesive termini. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3', single-stranded termini with their 3'–5' exonucleolytic activities and fill in recessed 3' ends with their polymerizing activities. The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies, Inc., New Haven, Conn.

Also contemplated by the present invention are RNA equivalents of the above described recombinant DNA molecules.

D. Transformed Cells and Cultures

The present invention also relates to a host cell transformed with a recombinant DNA molecule of the present invention. The host cell can be either procaryotic or eucaryotic. Bacterial cells are preferred procaryotic host cells and typically are a strain of *E. coli* such as, for example the *E. coli* strain DH5 available from Bethesda Research Laboratories, Inc., Bethesda, Md. Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61 and NIH Swiss mouse embryo cells NIH/3T3 available from the ATCC as CRL 1658.

A preferred transformed cell line is *E. coli* containing the recombinant DNA molecule HEL41, a culture of which has been deposited with the American Type Culture Collection (ATCC), Rockville, Md., on Jul. 7, 1987 and was assigned accession number 67456.

Transformation of appropriate host cells with a recombinant DNA molecule of the present invention is accomplished by well known methods that typically depend on the type of vector used. With regard to transformation of procaryotic host cells, see, for example, Cohen et al., *Proc. Natl. Acad. Sci. USA*, 69:2110 (1972); and Maniatis et al., *Molecular Cloning, A Laboratory Mammal*, Cold Spring Harbor Laboratory, Cold Spring Harbor, N.Y. (1982). With regard to transformation of vertebrate cells with retroviral vectors containing rDNAs, see, for example, Sorge et al., *Mol. Cell. Biol.*, 4:1730–37 (1984); Graham et al., *Virol.*, 52:456 (1973); and Wigler et al., *Proc. Natl. Acad. Sci. USA*, 76:1373–76 (1979).

Successfully transformed cells, i.e., cells that contain a recombinant DNA molecule of the present invention, can be identified by well known techniques. For example, cells resulting from the introduction of an rDNA of the present invention can be cloned to produce monoclonal colonies. Cells from those colonies can be harvested, lysed and their DNA content examined for the presence of the rDNA using a method such as that described by Southern, *J. Mol. Biol.*, 98:503 (1975) or Berent et al., Biotech., 3:208 (1985).

In addition to directly assaying for the presence of rDNA, successful transformation can be confirmed by well known immunological methods when the rDNA is capable of directing the expression of a GPIIb-related protein. For example, cells successfully transformed with an expression vector produce proteins displaying GPIIb antigenicity. Samples of cells suspected of being transformed are harvested and assayed for GPIIb-related protein using antibodies specific for those antigens, such as those produced by a hybridoma of the present invention.

Thus, in addition to the transformed host cells themselves, the present invention also contemplates a culture of those cells, preferably a monoclonal (clonally homogeneous) culture, or a culture derived from a monoclonal culture, in a nutrient medium. Preferably, the culture also contains a protein displaying GPIIb antigenicity.

Nutrient media useful for culturing transformed host cells are well known in the art and can be obtained from several commercial sources. In embodiments wherein the host cell is mammalian, a "serum-free" medium is preferably used.

E. Methods for Producing GPIIb-Related Proteins

Another aspect of the present invention pertains to a method for producing proteins displaying GPIIb antigenicity. Proteins that display GPIIb antigenicity are proteins that immunoreact with antibodies induced by native GPIIb. Proteins displaying GPIIb antigenicity are useful as antigens and for raising antibodies, each of which can be used in the diagnostic systems and methods of the present invention.

The present method entails initiating a culture comprising a nutrient medium containing host cells, preferably human cells, transformed with a recombinant DNA molecule of the present invention that is capable of expressing a gene encoding a GPIIb-related amino acid residue sequence. The culture is maintained for a time period sufficient for the transformed cells to express a protein containing a GPIIb-related amino acid residue sequence. The expressed protein is then recovered from the culture.

Methods for recovering an expressed protein from a culture are well known in the art and include fractionation of the protein-containing portion of the culture using well known biochemical techniques. For instance, the methods of gel filtration, gel chromatography, ultrafiltration, electrophoresis, ion exchange, affinity chromatography and the like, such as are known for protein fractionations, can be used to isolate the expressed proteins found in the culture. In addition, immunochemical methods, such as immunoaffinity, immunoadsorption and the like can be performed using well known methods.

F. Polypeptides

A polypeptide of the present invention contains no more than about 50, more usually fewer than about 35 and preferably fewer than about 25 amino acid residues, and contains at least about 10 residues. In addition, a polypeptide of the present invention is characterized by its amino acid residue sequence and novel functional properties.

1. hGPIIb Cryptic Determinant Polypeptide Analogs

Broadly, one embodiment of the present invention contemplates a polypeptide that includes an amino acid residue sequence capable of mimicking a cryptic antigenic determinant expressed by the heavy chain of the alpha subunit of an RDG-binding cytoadhesive protein. The amino acid residue sequence of the cryptic determinant polypeptide analog corresponds to the sequence of the about 15 carboxy terminal amino acid residues of the heavy chain of the alpha subunit of the cytoadhesin.

A preferred cytoadhesin alpha subunit heavy chain cryptic determinant polypeptide analog is capable of mimicking a hGPIIb cryptic determinant that is formed when hGPIIb binds fibrinogen. In preferred embodiments, a hGPIIb cryptic determinant polypeptide analog includes at least the following amino acid residue sequence:

—PAHHKRDRRQ—, representing amino acid residues 137–145 as shown in FIG. 1.

More preferably, a hGPIIb cryptic determinant polypeptide analog includes at least the following amino acid residue sequence:

—PSPSPIHPAHHKRDRRQ—, representing amino acid residues 129–145 as shown in FIG. 1.

Preferred hGPIIb cryptic determinant analogs include those whose amino acid residue sequences are shown in Table 1.

TABLE 1

| Designation[a] | Amino Acid Residue Sequence |
|---|---|
| p136–145 | PAHHKRDRRQ |
| p133–145 | PIHPAHHKRDRRQ |
| p131–145 | PSPIHPAHHKRDRRQ |
| p129–145 | PSPSPIHPAHHKRDRRQ |

[a]The designation of each polypeptide represents the included amino acid residue sequence as shown in FIG. 1.

The polypeptides shown in Table 1 are further characterized by their ability to neutralize (competitively inhibit) the binding of PMI-1 antibody molecules, described hereinbelow, with hGPIIb when hGPIIb is present as a GPIIb-IIIa/fibrinogen complex.

The word "complex" as used herein refers to the product of a specific binding reaction such as an antibody-antigen or receptor-ligand reaction. Exemplary complexes are immunoreaction products GPIIb-IIIa-fibrinogen binding reaction products, and cytoadhesin-ligand binding reaction products.

In preferred embodiments a hGPIIb cryptic determinant analog is further characterized by its ability to competitively inhibit the aggregation of fibrinogen-bound platelets. An exemplary hGPIIb cryptic determinant analog capable of inhibiting fibrinogen-bound platelet aggregation is polypeptide p129–145.

It should be understood that a hGPIIb cryptic determinant polypeptide analog of the present invention need not be identical to the amino acid residue sequence of hGPIIb, so long as it is able to competitively inhibit fibrinogen-bound platelet aggregation and/or is able to competitively inhibit the binding of PMI-1 antibody molecules, described hereinbelow, to hGPIIb when hGPIIb is present as a GPIIb-IIIa/fibrinogen complex. Therefore, a hGPIIb cryptic determinant polypeptide analog can be subject to various changes, such as insertions, deletions and substitutions, either conservative or non-conservative, where such changes provide for certain advantages in their use.

Conservative substitutions are those where one amino acid residue is replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like. The term "conservative substitution" also includes the use of a substituted amino acid in place of an unsubstituted parent amino acid provided that such a polypeptide also displays the requisite binding activity.

Amino acid residues present in a polypeptide of the invention in addition to a sequence specifically enumerated hereinafter up to a total of no more than about 50 amino acid residues can be any residues that do not materially affect the basic and novel characteristics of a polypeptide as are discussed hereinafter. Such additional residues are usually added to one or both termini of an enumerated polypeptide and can include repeats and partial repeats of an enumerated polypeptide sequence.

When a polypeptide of the present invention has a sequence that is not identical to the sequence of hGPIIb because one or more conservative or non-conservative substitutions have been made, usually no more than about 20% and more usually no more than 10% of the amino acid residues are substituted, except where additional residues have been added at either terminus for the purpose of providing a "linker" by which the polypeptides of this invention can be conveniently affixed to a label or solid matrix, or antigenic carrier. Labels, solid matrices and carriers that can be used with the polypeptides of this invention are described hereinafter.

Amino acid residue linkers are usually at least one residue and can be 40 or more residues, more often 1 to 10 residues. Typical amino acid residues used for linking are tyrosine, cysteine, lysine, glutamic and aspartic acid, or the like. In addition, a polypeptide sequence of this invention can differ from the natural sequence by the sequence being modified by terminal-NH$_2$ acylation, e.g., acetylation, or thioglycolic acid amidation, terminal-carboxlyamidation, e.g., ammonia, methylamine, etc.

When coupled to a carrier via a linker to form what is known in the art as a carrier-hapten conjugate, a hGPIIb cryptic determinant polypeptide analog of the present invention is capable of inducing antibodies that immunoreact with hGPIIb when hGPIIb is present as a platelet-associated GPIIb-IIIa/fibrinogen complex. In view of the well established principle of immunologic cross-reactivity, the present invention therefore contemplates antigenically related variants of the polypeptide p129–145. An "antigenically related variant" is a polypeptide that includes at least a six amino acid residue sequence portion of polypeptide p129–145 and which is capable of inducing antibody molecules that immunoreact with polypeptide p129–145 and hGPIIb when hGPIIb is present as a platelet-associated GPIIb-IIIa/fibrinogen complex.

2. 1GPIIb Polypeptides

In another embodiment, the present invention contemplates a 1GPIIb polypeptide that includes at least the following amino acid residue sequence:

$$-\text{RQIFLPEPEQPSR}-,$$

representing amino acid residues 144–156 as shown in FIG. 1.

A 1GPIIb polypeptide is further characterized by its ability to induce antibody molecules that immunoreact with 1GPIIb but do not immunoreact with hGPIIb. A preferred 1GPIIb polypeptide, designated p144–156, has an amino acid residue sequence represented by the formula:

RQIFLPEPEQPSR.

Both a hGPIIb and a 1GPIIb polypeptide of the present invention can be synthesized by any techniques that are known to those skilled in the polypeptide art. An excellent summary of the many techniques available may be found in J. M. Steward and J. D. Young, "Solid Phase Peptide Synthesis", W. H. Freeman Co., San Francisco, 1969, and J. Meienhofer, "Hormonal Proteins and Peptides", Vol. 2, p. 46, Academic Press (New York), 1983, for solid phase peptide synthesis, and E Schroder and K. Kubke, "The Peptides" Vol 1 Academic Press (New York), 1965, for classical solution synthesis.

G. Inocula

In another embodiment, a polypeptide of this invention or an antigenically related variant thereof is used in a pharmaceutically acceptable aqueous diluent composition to form an inoculum that, when administered in an effective amount, is capable of inducing antibodies that immunoreact with hGPIIb.

The word "inoculum" in its various grammatical forms is used herein to describe a composition containing a polypeptide of this invention as an active ingredient used for the preparation of antibodies against the heavy or light chain of GPIIb.

When a polypeptide is used to induce antibodies it is to be understood that the polypeptide can be used alone, or linked to a carrier as a conjugate, or as a polypeptide polymer, but for ease of expression the various embodiments of the polypeptides of this invention are collectively referred to herein by the term "polypeptide", and its various grammatical forms.

For a polypeptide that contains fewer than about 35 amino acid residues, it is preferable to use the peptide bound to a carrier for the purpose of inducing the production of antibodies as already noted.

As already noted, one or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, di-aldehydes such as glutaraldehyde, Klipstein et al., *J. Infect. Dis.*, 147, 318–326 (1983) and the like, or the use of carbodiimide technology as in the use of a water-soluble carbodiimide to form amide links to the carrier. For a review of protein conjugation or coupling through activated functional groups, see Auramneas, et al., *Scand. J. Immunol.*, Vol. 8, Supp-1. 7, 7–23 (1978).

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine: D-glutamic acid), and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide or protein per unit dose depends, among other things, on the species of animal inoculated, the body weight of the animal and the chosen inoculation regimen as is well known in the art. Inocula typically contain polypeptide or protein concentrations of about 10 micrograms to about 500 milligrams per inoculation (dose), preferably about 50 micrograms to about 50 milligrams per dose.

The term "unit dose" as it pertains to the inocula of the present invention refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent or vehicle such as water, saline or phosphate-buffered saline to form an aqueous composition. Such diluents are well known in the art and are discussed, for example, in *Remington's Pharmaceutical Sciences*, 16th Ed., Mack Publishing Company, Easton, Pa. (1980) at pages 1465–1467.

Inocula can also include an adjuvant as part of the diluent. Adjuvants such as complete Freund's adjuvant (CFA), incomplete Freund's adjuvant (IFA) and alum are materials well known in the art, and are available commercially from several sources.

H. Antibodies and Antibody Compositions

1. Antibody Compositions

The term "antibody" in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v).

An "antibody combining site" is that structural portion of an antibody molecule comprised of a heavy and light chain variable and hypervariable region(s) that specifically binds (immunoreacts with) antigen. The term "immunoreact" in its various forms is used herein to refer to binding between an antigenic determinant-containing molecule and a molecule containing an antibody combining site such as a whole antibody molecule or a portion thereof.

"Antigenic determinant" refers to the actual structural portion of the antigen that is immunologically bound by an antibody combining site. The term is also used interchangeably with "epitope".

An antibody composition of the present invention is characterized as containing antibody molecules that immunoreact with: a) hGPIIb or 1GPIIb, and b) at least one specific polypeptide of this invention. In a preferred embodiment, an antibody composition of this invention contains more than one species of paratope capable of immunoreacting with a GPIIb.

For instance, an antibody composition of the present invention containing antibody molecules that immunoreact with platelet-associated GPIIb-IIIa/fibrinogen complexes and a hGPIIb cryptic determinant polypeptide analog but do not substantially immunoreact with polypeptide p53–64, whose amino acid residue sequence is shown in Table 2, is capable of distinguishing fibrinogen-bound platelets from platelets that have not bound fibrinogen. Thus, preferred antibody compositions are those containing antibody molecules that immunoreact with: a) hGPIIb when it is present as a platelet-associated GPIIb-IIIa/fibrinogen complex, and b) polypeptide p129–145, and are substantially free from immunoreaction with polypeptide p53–64.

An antibody composition of the present invention is typically produced by immunizing a mammal with an inoculum of the present invention and thereby induce in the mammal antibody molecules having the appropriate polypeptide immunospecificity. The antibody molecules are then collected from the mammal and isolated to the extent desired by well known techniques such as, for example, by immunoaffinity chromatography. The antibody composition so produced can be used inter alia, in the diagnostic methods and systems of the present invention to detect fibrinogen-bound platelets in a body sample.

2. Monoclonal Antibody Compositions

An anti-LIBS monoclonal antibody composition is also contemplated by the present invention. The phrase "monoclonal antibody composition" in its various grammatical forms refers to a population of antibody molecules that contain only one species of antibody combining site capable of immunoreacting with a particular antigen. A monoclonal antibody composition thus typically displays a single binding affinity for any antigen with which it immunoreacts. A monoclonal antibody composition may therefore contain an antibody molecule having a plurality of antibody combining sites, each immunospecific for a different antigen, e.g., a bispecific monoclonal antibody.

A monoclonal antibody composition is typically composed of antibodies produced by clones of a single cell called a hybridoma that secretes (produces) but one kind of antibody molecule. The hybridoma cell is formed by fusing an antibody-producing cell and a myeloma or other self-perpetuating cell line. Such antibodies were first described by Kohler and Milstein, Nature 256:495–497 (1975), which description is incorporated by reference.

In one embodiment, a monoclonal antibody composition of the present invention is characterized as containing antibody molecules that immunoreact with a LIBS expressed by a cell surface receptor-ligand complex, preferably a cryptic antigenic determinant of the receptor in the complex.

In another embodiment, a monoclonal antibody composition contains antibody molecules that immunoreact with hGPIIb and a hGPIIb cryptic determinant polypeptide analog, preferably p129–145. The antibody molecules contained in these compositions immunoreact with hGPIIb at or near a GPIIb functional site but do not inhibit the binding of fibrinogen by platelet-associated GPIIb-IIIa and can immunologically react with platelet-associated GPIIb-IIIa when it has bound fibrinogen. A preferred monoclonal antibody composition of this type contains antibody molecules capable of being produced by hybridoma PMI-1 (ATCC HB 9476), i.e., PMI-1 antibody molecules.

3. Methods for Producing mAb Compositions

The present invention contemplates a method of forming a monoclonal antibody molecule that (a) immunoreacts with a ligand-induced binding site (LIBS) expressed by a cell surface receptor-ligand complex, and (b) does not immunoreact with either the non-occupied receptor or the non-bound ligand of the receptor-ligand complex. The method comprises the steps of:

(a) Immunizing an animal with a cell surface-receptor complex or a hGPIIb cryptic determinant polypeptide analog. This is typically accomplished by administering an immunologically effective amount i.e., an amount sufficient to produce an immune response, of immunogen to an immunologically competent mammal. Preferably, the mammal is a rodent such as a rabbit, rat or mouse. The mammal is then maintained for a time period sufficient for the mammal to produce cells secreting antibody molecules that immunoreact with the receptor-ligand complex.

(b) A suspension of antibody-producing cells removed from the immunized mammal is then prepared. This is typically accomplished by removing the spleen of the mammal and mechanically separating the individual spleen cells is a physiologically tolerable medium using methods well known in the art.

(c) The suspended antibody producing cells are treated with a transforming agent capable of producing a transformed ("immortalized") cell line. Transforming agents and their use to produce immortalized cell lines are well known in the art and include DNA viruses such as Epstein Bar Virus (EBV), Simian Virus 40 (SV40), Polyoma Virus and the like, RNA viruses such as Moloney Murine Leukemia Virus (Mo-MuLV), Rous Sarcoma Virus and the like, myeloma cells such as P3×63-Ag8.653, Sp2/O-Ag14 and the like.

In preferred embodiments, treatment with the transforming agent results in the production of a hybridoma by fusing the suspended spleen cells with mouse myeloma cells from a suitable cell line by the use of a suitable fusion promoter. The preferred ratio is about 5 spleen cells per myeloma cell in a suspension containing about $10^8$ splenocytes.

The cell line used should preferably be of the so-called "drug resistant" type, so that unfused myeloma cells will not survive in a selective medium, while hybrids will survive. The most common class is 8-azaguanine resistant cell lines, which lack the enzyme hypoxanthine-guanine phosphoribosyl transferase and hence will not be supported by HAT (hypoxanthine, aminopterin, and thymidine) medium. It is also generally preferred that the myeloma cell line used be of the so-called "non-secreting" type which does not itself produce any antibody, although secreting types may be used.

In certain cases, however, secreting myeloma lines may be preferred. While the preferred fusion promoter is polyethylene glycol having an average molecule weight from about 1000 to about 4000 (commercially available as PEG 1000, etc.), other fusion promoters known in the art may be employed.

(d) The transformed cells are then cloned, preferably to monoclonality. The cloning is preferably performed in a tissue culture medium that will not sustain (support) non-transformed cells. When the transformed cells are hybridomas, this is typically performed by diluting and culturing in separate containers the mixture of unfused spleen cells, unfused myeloma cells, and fused cells (hybridomas) in a selective medium which will not support (sustain) the unfused myeloma cells for a time sufficient to allow death of the unfused cells (about one week). The dilution may be a type of limiting dilution, in which the volume of diluent is statistically calculated to isolate a certain number of cells (e.g., 1–4) in each separate container (e.g., each well of a microtiter plate). The medium is one (e.g., HAT medium) which will not support the drug-resistant (e.g., 8-azaguanine resistant) unfused myeloma cell line.

(e) The tissue culture medium of the cloned transformants is evaluated for the presence of secreted anti-LIBS antibody molecules using well known immunological techniques.

(f) Once a desired transformant has been identified in step (e), it is selected and grown in a suitable tissue culture medium for a suitable length of time, followed by recovery of the desired antibody from the culture supernatant. The suitable medium and suitable length of culturing time are known or are readily determined.

To produce a much greater concentration of slightly less pure monoclonal antibody, the desired hybridoma may be injected into mice, preferably syngenic or semisyngenic mice. The hybridoma will cause formation of antibody-producing tumors after a suitable incubation time, which will result in a high concentration of the desired antibody (about 5–20 mg/ml) in the bloodstream and peritoneal exudate (ascites) of the host mouse.

Media useful for the preparation of these compositions are both well known in the art and commercially available and include synthetic culture media, inbred mice and the like. An exemplary synthetic medium is Dulbecco's minimal essential medium [DMEM; Dulbecco et al., *Virol.* 8:396 (1959)] supplemented with 4.5 gm/l glucose, 20 mm glutamine, and 20% fetal calf serum. An exemplary inbred mouse strain is the Balb/c.

The monoclonal antibody compositions produced by the above method can be used, for example, in diagnostic and therapeutic modalities wherein formation of a LIBS-containing immunoreaction product is desired. Exemplary reaction products include a GPIIb or a GPIIIa-containing immunoreaction product.

I. Hybridomas and Methods of Preparation

Hybridomas of the present invention are those which are characterized as having the capacity to produce an anti-LIBS monoclonal antibody composition.

A preferred hybridoma of the present invention is characterized as producing antibody molecules that immunoreact with a cell surface receptor cryptic antigenic determinant.

Methods for producing hybridomas producing (secreting) antibody molecules having a desired immunospecificity, i.e., having the ability to immunoreact with a particular protein, an identifiable epitope on a particular protein and/or a polypeptide, are well known in the art. Particularly applicable is the hybridoma technology described by Niman et al., *PNAS USA* 80:4949–4953 (1983), and by Galfre et al., *Meth. Enzymol.* 73:3–46 (1981), which descriptions are incorporated herein by reference. Shadle, et al., *J. Cell. Bio.* 99:2056–60 (1984), which describes the production of hybridomas PMI-1 and PMI-2, is also incorporated by reference herein.

Hybridoma culture PMI-1 has been deposited pursuant to Budapest Treaty requirements with the American Type Culture Collection (ATCC), Rockville, Md. 20852, USA, on Jul. 7, 1987, and was assigned accession number HB 9476. Hybridoma culture PMI-2 was similarly deposited with the ATCC on Dec. 22, 1987, and was assigned accession number HB 9615.

J. Therapeutic Methods and Compositions

A hGPIIb cryptic determinant polypeptide analog of the present invention can be used to modulate the aggregation of fibrinogen-bound platelets in vivo.

For instance, a hGPIIb cryptic determinant polypeptide analog can be used in a pharmaceutically acceptable composition that, when administered to a human subject in an effective amount, is capable of competitively inhibiting the aggregation of fibrinogen-bound platelets. That inhibition is believed to result in a decreased rate of thrombus formation. Thus, in vivo administration of a hGPIIb cryptic determinant polypeptide analog can be used to modulate any physiological response initiated by platelet aggregation such as coagulation and some inflammatory responses.

In another embodiment, the aggregation of fibrinogen-bound platelets can be inhibited by intravenous administration of an effective amount of a pharmaceutically acceptable composition consisting essentially of antibody molecules that immunoreact with a hGPIIb cryptic determinant polypeptide analog, preferably p129–145. Preferably, the antibody molecules are present as a monoclonal antibody composition and more preferably are those produced by hybridoma PMI-1.

The polypeptide- or antibody molecule-containing compositions administered take the form of solutions or suspensions, however, polypeptides can also take the form of tablets, pills, capsules, sustained release formulations or powders. In any case, the compositions typically contain about 0.1 µM to about 1.0M of active ingredient, preferably about 1.0 µM to about 10 millimolar (mM).

The preparation of a therapeutic composition that contains polypeptides or antibody molecules as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient as are well known. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide or antibody molecule composition can be formulated into the therapeutic composition as neutralized pharmaceutically acceptable salt forms. Pharmaceutically acceptable salts include the acid addition salts (formed with the free amino groups of the polypeptide or antibody molecule) that are formed with inorganic acids such as, for example, hydrochloric or phosphoric acids, or such organic acids as acetic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide- or antibody molecule-containing compositions are conventionally administered intravenously, as by injection of a unit dose, for example. The term "unit dose" when used in reference to a therapeutic composition of the present invention refers to physically discrete units suitable as unitary dosages for humans, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject to utilize the active ingredient, and degree of inhibition of receptor-ligand binding desired. Precise amounts of active ingredient required to be administered depend on the judgment of the practitioner and are peculiar to each individual. However, suitable dosage ranges are of the order of one to several milligrams of active ingredient per individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain therapeutically effective concentrations in the blood are contemplated. For a hGPIIb cryptic determinant polypeptide, therapeutically effective blood concentrations are in the range of about 0.1 mM to about 10 mM, preferably about 1.0 mM. Therapeutically effective blood concentrations of antibody molecules of the present invention are in the range of about 0.1 uM to about 10 uM, preferably 1.0 uM.

K. Diagnostic Systems

A diagnostic system in kit form of the present invention includes, in an amount sufficient for at least one assay, an expressed protein, polypeptide, antibody composition or monoclonal antibody composition of the present invention, as a separately packaged reagent. Instructions for use of the packaged reagent are also typically included.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In one embodiment, a diagnostic system for assaying for fibrinogen-bound platelets in a platelet-containing vascular fluid sample, such as blood or plasma, comprises a package containing molecules that immunoreact with a hGPIIb cryptic determinant polypeptide analog, preferably p129–145. More preferably, the antibody molecules are those produced by hybridoma PMI-1 that immunoreact with hGPIIb. Preferably, the antibody molecules are present as a monoclonal antibody composition. Further preferred are kits wherein the antibody molecules are linked to a radionuclide label, preferably $^{125}$I-labeled PMI-1 antibody molecules.

In another embodiment, a diagnostic system of the present invention is useful for assaying for the presence of a thrombus in vivo. The system comprises a package containing antibody molecules that immunoreact with a hGPIIb cryptic determinant polypeptide analog, preferably p129–145. More preferably, the antibody molecules are present as a monoclonal antibody composition consisting essentially of PMI-1 antibody molecules that immunoreact with hGPIIb. The antibody molecules are linked to an in vivo indicating means.

Thus, in preferred embodiments, a diagnostic system of the present invention further includes a label or indicating means capable of signaling the formation of a complex containing an antibody molecule or polypeptide of the present invention.

As used herein, the terms "label" and "indicating means" in their various grammatical forms refer to single atoms and molecules that are either directly or indirectly involved in the production of a detectable signal to indicate the presence of a complex. "In vivo" labels or indicating means are those useful within the body of a human subject and include $^{111}$In, $^{99}$Tc, $^{67}$Ga, $^{186}$Re, and $^{132}$I. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel protein methods and/or systems.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., Meth. Enzymol., 73:3–46 (1981). The techniques of protein conjugation or coupling through activated functional groups are particularly applicable. See, for example, Aurameas, et al., Scand. J. Immunol., Vol. 8 Suppl. 7:7–23 (1978), Rodwell et al., Biotech.., 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention but is not itself a protein expression product, polypeptide, or antibody molecule of the present invention. Exemplary specific binding agents are antibody molecules, complement proteins or fragments thereof, protein A and the like. Preferably, the specific binding agent can bind the antibody molecule or polypeptide of this invention when it is present as part of a complex.

In preferred embodiments the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the presence or quantity of fibrinogen-bound platelets in a body fluid sample such as serum, plasma or urine. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090; No. 3,850, 752; and No. 4,016,043, which are all incorporated herein by reference.

Thus, in preferred embodiments, the expressed protein, polypeptide, or antibody molecule of the present invention can be affixed to a solid matrix to form a solid support that is separately packaged in the subject diagnostic systems.

The reagent is typically affixed to the solid matrix by adsorption from an aqueous medium although other modes of affixation, well known to those skilled in the art can be used.

Useful solid matrices are well known in the art. Such materials include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packages discussed herein in relation to diagnostic systems are those customarily utilized in diagnostic systems. Such packages include glass and plastic (e.g., polyethylene, polypropylene and polycarbonate) bottles, vials, plastic and plastic-foil laminated envelopes and the like.

L. Assay Methods

The present invention contemplates any method that results in detecting GPIIb, and particularly a complex containing fibrinogen-bound GPIIb as is found in a thrombus or in fibrinogen-bound platelets, by producing a complex containing an expressed protein, polypeptide or antibody molecule contained in an antibody or monoclonal antibody composition of the present invention. Those skilled in the art will understand that there are numerous well known clinical diagnostic chemistry procedures that can be utilized to form those complexes. Thus, while exemplary assay methods are described herein, the invention is not so limited.

1. Thrombus Detection

A method for detecting the presence of a thrombus in a human subject is contemplated. An effective amount of an antibody composition or a monoclonal antibody composition of the present invention containing anti-hGPIIb antibody molecules linked to an in vivo indicating means is intravenously administered into the subject. In preferred embodiments the labeled antibody molecules are those that immunoreact with hGPIIb and polypeptide p129–145 but not p53–64, more preferably those produced by hybridoma PMI-1.

The subject is then maintained for a predetermined time period sufficient for the labeled antibody molecules to react with hGPIIb present as part of a thrombus and form a complex, and preferably for an additional time period sufficient for a substantial amount of any non-reacted antibody molecules to clear the body. The subject is then assayed for the presence and preferably location of any labeled complex that formed.

2. Detection of Fibrinogen-Bound Platelets in a Body Sample

Various heterogeneous and homogeneous assay protocols can be employed, either competitive or non-competitive, for detecting the presence and preferably amount of fibrinogen-bound platelets in a platelet-containing body sample, preferably a body fluid sample such as blood or a platelet-containing portion of blood. For example, a heparin-preserved (non-clotted) blood sample and $^{125}$I-labeled PMI-1 antibody molecules are admixed. The immunoreaction admixture thus formed is maintained under biological assay conditions for a time period sufficient for any fibrinogen-bound platelets to immunoreact with the labeled antibodies and form a labeled immunoreaction product. The labeled immunoreaction products are then separated from the non-reacted labeled-antibodies, typically by centrifugation sufficient to pellet all platelets present in the sample. The amount of labeled immunoreaction product formed is then assayed.

Biological assay conditions are those that maintain the biological activity of the antibody molecules and polypeptide molecules of this invention and the fibrinogen-bound platelets sought to be assayed. Those conditions include a temperature range of about 4 degrees C. to about 45 degrees C., preferably about 37 degrees C., a pH value range of about 5 to about 9, preferably about 7 and an ionic strength varying from that of distilled water to that of about one molar sodium chloride, preferably about that of physiological saline. Methods for optimizing such conditions are well known in the art.

EXAMPLES

The following examples are intended to illustrate, but not limit, the present invention.

1. Isolation of GPIIb-IIIa

A. Platelet Isolation

Sixty milliliters (ml) of whole human blood was collected in 5 ml of ACD (0.065M citric acid, 0.085M sodium citrate, 2% dextrose) containing hirudin (Sigma Chemical Co., St. Louis, Mo.) at a final concentration of 0.06 units per milliliter (U/ml) and centrifuged for 15 minutes at 120 xg. The resulting supernatant, designated platelet rich plasma (PRP), was recovered, isolated and further centrifuged for 15 minutes at 1200 xg to form a pellet of isolated platelets.

B. GPIIb-IIIa Isolation from Platelets

A platelet pellet prepared as in Example 1A, was resuspended in 5 ml TBS (0.15M NaCl, 0.2M Tris, pH 7.4, $5 \times 10^{-4}$M $CaCl_2$, $10^{-5}$M leupeptin) and sonicated on ice for 10 minutes at a maximum setting using a Model W-375 sonicator (Heat Systems Ultrasonics, Plainview, N.Y.). The sonicated suspension was twice frozen and thawed using a dry ice-methanol ice bath and stored at minus 20 degrees C. The frozen-thawed platelet sonicate was layered on top of 5 ml of a sucrose solution (40 % v/v in TBS), and centrifuged at 4 degrees C. for one hour at 38,000 rotations per minute (RPM) in a SW41 centrifuge rotor (Beckman Instruments, Fullerton, Calif.) to form a milky colored infranatant. The milky-infranatant was then recovered and centrifuged at 43,000 RPM in a SW50.1 centrifuge rotor (Beckman) at 4 degrees C. for one hour. The resulting pellet was resuspended in typically 1–2 ml TBS to form a platelet membrane solution, the protein concentration of which was determined to be in the range of 10–25 mg/ml, typically using the Bio-Rad Protein Assay Kit (BioRad, Richmond, Calif.) according to the manufacturer's instructions.

The platelet membrane solution was again centrifuged in a SW50.1 centrifuge rotor as above and the resulting pellet was resuspended in 2 ml of extraction buffer (0.03 M Tris, pH 7.4, 1×10$^{-5}$M leupeptin, 200 mM n-octyl-beta-D-glucopyranoside; Calbiochem-Behring, La Jolla, Calif.). The platelet membrane extract thus formed was admixed thoroughly by vortexing and then maintained at room temperature for 30 minutes. The extract was thereafter centrifuged at 45,000 rpm in a SW50.1 centrifuge rotor for 1 hour at 4 degrees C. and the platelet membrane extract supernatant thus formed was recovered.

The recovered supernatant was applied to a LKB Ultrogel Aca 34 gel filtration column (3×97 cm, LKB Instruments, Gaithersburg, Md.) that had been equilibrated with 1 liter of column buffer (0.03M Tris, pH 7.4, 0.1 mM CaCl$_2$, 0.1% n-octyl-beta-D-glucopyranoside) and 5 ml fractions were collected from the resulting column effluent. The optical density at 280 nanometers of each fraction was determined and fractions around the several peaks were combined to form a pool for each peak. Samples from each pool were analyzed by electrophoresis in 6% polyacrylamide slab gels using the reducing buffers and procedures described by Laemmli, Nature (London).., 27:680–685 (1970), and low molecular weight protein standards ranging in size from 14.4 kilodaltons (KDa) to 92.5 KDa (Bio-Rad, Richmond, Calif.). The pool containing predominantly two protein species having molecular weights corresponding to GPIIb and GPIIIa, i.e., 120 KDa and 100 KDa, respectively was recovered. The protein concentration of the isolated GPIIb-IIIa preparation thus prepared was typically determined using the Bio-Rad Protein Assay Kits to be in the range of 0.3 to 0.8 mg/ml 2. Preparation of Polyclonal Anti-GPIIb-IIIa Antiserum Rabbit anti-GPIIb-IIIa antibodies were prepared by immunization with a composition containing complete Freund's Adjuvant and 100 micrograms (ug) of isolated GPIIb-IIIa protein, prepared as described in Example 1. Booster injections of GPIIb-IIIa were administered at multiple intradermal sites (typically 100 ug distributed over 4 sites) in incomplete Freund's adjuvant on a weekly schedule for three weeks followed by a biweekly schedule for an additional three months.

3. cDNA Library Construction, Antibody Screening and Identification of cDNA Clones Total cellular RNA was prepared from HEL cells by the guanidinium isothiocyanate/cesium chloride method. Poly (A$^+$)RNA was purified from the total RNA fraction by two cycles of chromatography on oligo (dT) cellulose. Double stranded cDNA was synthesized from 10 ug HEL poly (A$^+$)RNA using AMV reverse transcriptase (Life Sciences, Inc., St. Petersburg, Fla.) and random oligodeoxynucleotide primers according to standard procedures. Size selected cDNA was ligated into the EcoRI site of phage gt11, packaged into the phage according to the manufacturer's protocol using the Gigapack packaging extract available from Stratagene Cloning Systems, San Diego, Calif., and then plated and amplified on E. coli Y1088. Plating of phage on E. coli Y1090, induction of fusion protein synthesis, transfer to nitrocellulose filters, and screening of the filters with the rabbit polyclonal GPIIb-IIIa antiserum prepared in Example 2 was performed as described by Young et al., Proc. Natl. Acad. Sci. USA, 80:1194–1198 (1983) using the immunoperoxidase based Vectastain ABC method (Vector Laboratories, Burlingame, Calif.) according to manufacturer's instructions. Positive recombinant clones were plaquepurified, amplified and collected as a plate lysate.

Initial screening of 200,000 recombinants with the rabbit polyclonal GPIIb-IIIa antiserum identified six immunoreactive clones. To examine the immunoreactivity of the beta-galactosidase-cDNA fusion protein of positive clones with the monoclonal antibody PMI-1, phage lysogens were produced in E. coli strain Y1089 as described by Young et al., Science, 222:778–782 (1983). Lysates from IPTG induced cultures were prepared by resuspending the bacterial cell pellets in reducing gel sample buffer after which the samples were run on 6% SDS-polyacrylamide gels, transferred to nitrocellulose as described by Towbin et al., Proc. Natl. Acad. Sci. USA, 26:4350–4354 (1979), and probed with PMI-1 using the Vecastain ABC method.

One of these clones, HEL41, that contained a 1.1 kilobases (Kb) insert, was found to direct the synthesis of a bacterial fusion protein of 140 KDa having characteristics consistent with it possessing GPIIb epitopes. Those characteristics included: (1) blockable reactivity of the polyclonal anti-GPIIb-IIIa antibody composition with the fusion protein encoded by the HEL41 clone was blocked by prior absorption with isolated GPIIb-IIIa; (2) specific reaction of antibodies affinity-purified on the fusion protein with GPIIb in immunoblots of platelet lysates and purified GPIIb-IIIa; and (3) immunoprecipitation of GPIIb-IIIa from surface labeled platelets by the affinity purified antiserum. The affinity purified antibody failed to react with the alpha subunit of the vitronectin receptor (VnR) by Western blotting and failed to immunoprecipitate the related endothelial cell cytoadhesin. In addition, the fusion protein encoded by HEL41 was immunoreactive with the monoclonal antibody PMI-1 providing further evidence that this clone encoded epitopes available on GPIIb.

4. DNA Sequencing and Sequence Analysis

Recombinant phage DNA from HEL41 was purified by the liquid culture technique, digested with EcoRI and subcloned into M13mp18. The DNA sequence for each strand was determined by the dideoxy chain termination method of Sanger et al., Proc. Natl. Acad. Sci. USA, 74:5463–5467 (1977) using $^{35}$S-dATp and buffer gradient gels described by Biggin et al., Proc. Natl. Acad. Sci. USA, 80:3963–3965 (1983). The cDNA sequence was extended using the specific primer-directed DNA sequencing method as described by Strauss et al., Anal. Biochem., 154:353–360 (1986). Oligonucleotide 20 mer sequencing primers were synthesized on an Applied Biosystems Model 380A DNA Synthesizer. Both strands were sequenced to resolve ambiguities.

The nucleotide sequence of clone HEL41 is shown in FIG. 1 and has the following features. The insert consists of an open reading frame of 681 bases with a TAG termination codon beginning at position 682 followed by 420 bases of 3' untranslated sequence. The first 120 nucleotides at the 5' end of the clone possess the characteristics of the consensus Alu repetitive sequence indicating this clone may have been derived from an incompletely processed mRNA.

The cDNA sequence of clone HEL41 encodes an open reading from of 227 amino acids (FIG. 1). The determined N-terminal sequence for the light chain of GPIIb, as reported by Charo et al. Proc. Natl. Acad. Sci. USA, 83:8351–8356 (1976), can be identified within the clone as amino acid residues 157 to 171. The consensus Alu repetitive sequence translates in frame and accounts for the first 40 amino acid residues encoded by HEL41.

Comparison of the deduced amino acid sequences of GPIIb and VnR alpha subunits [Suzuki et al., Proc. Natl. Acad. Sci. USA, 83:8614–8618 (1986)] by matrix analysis [George et al., PIR Report #REL0286, National Biomedical Research Foundation (1986)] detected two regions of similarity allowing for conservative substitutions. One region, encompassing approximately 50 amino acid residues, is located near the carboxyl-terminus of the heavy chains. The second region of about 15 residues is located near the amino-terminus of the light chains and includes cysteine residues which may be involved in forming disulfide bonds between the heavy and light chains of both proteins. Evaluation of the statistical significance of the relationship between the sequence of GPIIb and VnR alpha subunits with the Relate program employing the mutation data matrix indicated a low probability of finding this degree of similarity present in the two sequences by chance (p<0.0001). Analysis of the relationship between the sequence of GPIIb and FnR alpha subunits [Argraves et al., *J. Biol. Chem.*, 261:12922–12924 (1986)] indicated a similar low probability of finding the degree of similarity present in the two sequences by chance (P<0.0005).

A computer search revealed no other evident similarities between this portion of GPIIb and other sequences present in the NBRF protein database. In addition, no significant identities were detected in a direct comparison with the published partial sequence for the neural cell adhesion molecule, N-CAM.

5. Polypeptide Synthesis

Based on the amino acid residue sequence deduced from the nucleotide sequence, polypeptides corresponding to the various GPIIb regions utilized herein were chemically synthesized on an Applied Biosystems Model 430A Peptide Synthesizer using the symmetrical anhydride method of Hagenmaier, et al., Hoppe-Seyler's Z. Phisiol. Chem., 353:1973 (1982).

The amino acid residue sequences of the polypeptides synthesized and their location within the deduced amino acid residue sequence of GPIIb as shown in FIG. 1 are listed in Table 2.

TABLE 2

| Designation | Amino Acid Residue Sequence |
| --- | --- |
| p19–34 | WEAKAGRSPEVRSSRS |
| p53–65 | REQNSLDSWGPKV |
| p129–145 | PSPSPIHPAHHKRDRRQ |
| p136–145 | PAHHKRDRRQ |
| p144–156 | RQIFLPEPEQPSR |

6. Preparation of Monoclonal Antibody Compositions

Monoclonal antibody compositions comprised of isolated immunoglobulin IgG (IgG) were isolated from the ascites fluid of a mouse containing the mouse hybridoma cell line PMI-1 (ATCC number. HB 9476) using protein A-Sepharose typically obtained from Pharmacia Inc. (Piscataway, N.J.) and used according to manufacturer's instructions. The protein concentration of the isolated IgG was determined using the Bio-Rad Protein Assay Kit (Bio-Rad, Richmond, Calif.) according to the manufacturer's instructions.

To prepare a PMI-1 monoclonal antibody composition containing $^{125}$I-labeled antibody molecules, 350 microliters (ul) of PBS (0.15M NaCl, 0.01M sodium phosphate, pH 7.09) containing 1 milligrams per milliliter (mg/ml) of the above isolated PMI-1 IgG were admixed with 40 micrograms (ug) of chloramine-T and 1 milliCurie (mCi) of carrier-free Na$^{125}$I (Amersham, Arlington Heights, Ill.). The resulting admixture was maintained for 5 minutes at about 20 degrees C. and then admixed with 20 ul of a 2 mg/ml sodium metabisulfite solution (2 mg/ml) and 20 ul of a potassium iodide solution. Thereafter, 800 ul of PBS containing 1% BSA were admixed followed by further admixture of diisopropylfluorophosphate to a final concentration of 10 mM. The resulting admixture was maintained for 60 minutes at 22 degrees C. and then dialized against PBS. The specific activity of the resulting $^{125}$I-labeled PMI-1 was about 4.5 microCurie (uCi) per ug.

Compositions containing Fab fragments from the above isolated IgG were prepared by digestion with papain (200:1 weight per weight of IgG to papain) for 6 hours at 37 degrees C. following the methods of Mage et al., *Methods in Enzymology*, 70:142–150 (1980). Undigested IgG and Fc fragment were removed by chromatography on protein A-Sepharose. The resulting Fab fragment—containing compositions were then ready for use, or were $^{125}$I-labeled, as needed, using the same procedures as described above for monoclonal antibody compositions.

Monoclonal antibody compositions of the present invention having different immunospecificity than that of PMI-1 are also prepared as described above for PMI-1. For example, such compositions were prepared using the mouse hybridoma cell line PMI-2 (ATCC number HB 9615).

7. ELISA Assays

A. Polypeptide ELISA

Antibody molecules contained in PMI-1 and Tab monoclonal antibody compositions were examined for their ability to immunoreact with polypeptides p129–145 and p144–156. (Tab is an unrelated monoclonal antibody used as a control.) Fifty microliters (ul) of coating solution (0.1M NaHCO$_3$, pH 8.5, 0.1% NAN$_3$) containing 20 uM of polypeptide were admixed into the wells of flat-bottom 96-well microtiter plates (Immulon 2; Dynatech Laboratories, Chantilly, Va.). The plates were then maintained for 60 minutes at 37 degrees C. to permit the polypeptide to adsorb onto the walls of the wells. The coating solution was removed by shaking, the wells were rinsed twice with washing buffer (0.01M Tris, pH 7.4, 0.05% Tween 20, 0.15M NaCl, 200 mg/ml merthiolate), and 50 ul of blocking solution [5% bovine serum albumin (BSA;w/v) in coating solution] were admixed into each well (solid support) to block excess protein sites.

The wells were maintained for 60 minutes at about 37 degrees C. and then the blocking solution was removed. Into each well was admixed 50 ul of a solution containing (a) rabbit anti-polypeptide antibody, prepared in Example 8 and diluted 1:200 in dilution buffer (washing buffer containing 5 mM EDTA and 1 mg/ml BSA), (b) 1.5 nanomolar (nM), PMI-1 monoclonal antibody IgG prepared as described in Example 6, or (c) TAB hybridoma ascites fluid (provided by Dr. R. McEver, Universtiy of Texas, San Antonio, Tex.) diluted 1:320,000 in dilution buffer. The resulting solid/liquid phase immunoreaction admixtures were maintained at room temperature for 60 minutes to permit formation of a first solid phase-bound immunoreaction product between the solid phase-bound polypeptide and admixed antibodies. The solid and liquid phases were then separated, the wells were rinsed twice with washing buffer, and excess liquid was removed by shaking.

Fifty ul of a solution containing horseradish peroxidase labeled goat anti-mouse IgG (Tago Inc., Burlingame, Calif.), diluted 1:2000 in dilution buffer, or goat anti-rabbit IgG (Bio-Rad Laboratories, Inc., Richmond, Calif.), diluted 1:2000 in dilution buffer, was admixed into each well to form a second solid/liquid phase immunoreaction admixture (labeling immunoreaction admixture). The wells were maintained for 50 minutes at room temperature to permit formation of a second immunoreaction product between the labeled antibody and any solid phase-bound antibody of the first immunoreaction product and then rinsed twice with washing buffer to isolate the solid phase-bound label-containing immunoreaction products. Excess liquid was then removed from the wells.

Fifty ul of chromogenic substrate solution containing 0.4 mg/ml o-phenylenediamine and 0.012% (v/v) hydrogen peroxide in CP buffer (243 ml 0.1M citric acid and 250 ml 0.2M dibasic sodium phosphate per liter $H_2O$) were then admixed into each well to form a color developing-reaction admixture. After maintaining the developing-reaction admixture for 10 minutes at about 20 degrees C., 50 ul of 2N $H_2SO_4$ were admixed into each well to stop the developing-reaction, and the resulting solutions were assayed for adsorbance at 490 nanometers (nm) light wavelength using a model 310 ELISA plate reader (Bio-Tek Instruments, Winooski, Vt.).

The results of this study, shown in Table 3, demonstrate that monoclonal antibody PMI-1 immunoreacts with polypeptide p129–145 but does not immunoreact with polypeptide p144–156. Because PMI-1, as discussed hereinbelow, immunoreacts with a cryptic determinant formed by (exposed on) hGPIIb when GPIIb-IIIa binds fibrinogen, the results of this study indicate that p129–145 has the ability to mimic that hGPIIb cryptic determinant.

TABLE 3

| Polypeptide Antigen | Monoclonal Antibody | |
| --- | --- | --- |
| | PMI-1 | Tab |
| p129–145 | 1.310 ± 0.13[2] | 0.068 ± 0.009 |
| p144–156 | 0.069 ± 0.005 | 0.061 ± 0.005 |
| BSA[1] | 0.068 ± 0.005 | 0.060 ± 0.004 |

[1]BSA = bovine serum albumin coated wells used as negative control.
[2]Average optical density values ± standard deviation obtained from triplicate assays.

B. Competition ELISA

Polypeptides and isolated GPIIb-IIIa were examined for their ability to compete as antigen with solid-phase GPIIb-IIIa for immunoreaction with antibody molecules contained in PMI-1 and Tab monoclonal antibody compositions.

The competition ELISA was performed as described in Example 7A except that 1) instead of polypeptide, GPIIb-IIIa, isolated as described in Example 1, was used at 20 ug/ml in coating solution to coat the microtiter plate wells, and 2) GPIIb-IIIa or polypeptide was admixed at a concentration of 0.73 uM or 25 uM, respectively, to the wells immediately before antibody was admixed to form the immunoreaction admixture.

The results of this study, shown in Table 4, demonstrate that whereas p129–145 and GPIIb-IIIa 15 competitively inhibit the immunological binding of PMI-1 antibody molecules to solid-phase GPIIb-IIIa, p144–156 does not. In addition, neither polypeptide was found to have a significant effect on the ability of Tab antibody molecules to immunoreact with GPIIb-IIIa. These results indicate that polypeteide p129–145 has the ability to mimic the secondary structure and antigenic determinants of the hGPIIb region containing the p129–145 amino acid residue sequence.

TABLE 4

| Competitor | Monoclonal Antibodies | |
| --- | --- | --- |
| | PMI-1 | Tab |
| p129–145 | 0.067 ± 0.002[1] | 1.002 ± 0.026 |
| p144–156 | 0.814 ± 0.012 | 1.117 ± 0.024 |
| None | 0.804 ± 0.002 | 1.040 ± 0.05 |
| GPIIb-IIIa | 0.433 ± 0.013 | 0.134 ± 0.010 |

[1]Average optical density values ± standard deviation obtained from triplicate assays.

8. Preparation of Anti-peptide Antisera

Anti-peptide antibodies were produced by immunization of rabbits with the peptides prepared in Example 5. Coupling of the peptides with glutaraldehyde to thyroglobulin as antigenic carrier (Bovine Type I, Sigma Chemical Co., St. Louis, Mo.) was conducted as described by J. G. Dockray, *Regulatory. Peptides,* 1:169–186 (1980), which reference is hereby incorporated by reference. Thereafter immunization was conducted as described in Example 2 except that 400 ug of thyroglobulin-coupled peptide was used in the primary immunization.

9. Inhibition of Antibody Binding to Platelet-Associated GPIIb by Polypeptides

A. Platelet Preparation

Isolated platelets, prepared as in Example 1A, were resuspended in 2 ml of a calcium-free Tyrodes buffer (0.13M NaCl, 0.0026M KCl, 0.002M $MgCl_2$-$6H_2O$, 5 mM Hepes, 0.012M $NaHCO_3$, pH 7.2) containing 1 mg/ml BSA and 1 mg/ml dextrose. The platelet suspension was then applied to a Sepharose CL2B column (40 ml total bed volume, Pharmacia Inc., Piscataway, N.J.) equilibrated with the same Tyrodes' buffer. Platelets were recovered from the void volume of the CL2B column in a final volume of about 4 to 5 ml, were designated washed platelets and suspensions of the resulting washed platelets and were counted with a Coulter Model II counter (Coulter Electronics, Inc. Hialeah, Fla.). The entire platelet preparation procedure was performed in plastic containers and carried out at room temperature.

B. Platelet Competition Assay

Washed platelets ($2 \times 10^8$/ml) prepared in Tyrode's buffer as described in Example 9A were admixed with ethylenediaminetetraacetic acid (EDTA) so as to produce a final concentration of 5 mM and were maintained for 30 minutes at 37 degrees C. to permit exposure of the PMI-1-binding epitope. The platelets were then admixed with polypeptide p129–145 at the concentrations indicated in FIG. 2, and then further admixed with $^{125}$I-labeled PMI-1 prepared in Example 6 to produce 1 uM labeled antibody in the resulting immunoreaction admixture. That admixture was maintained for 30 minutes at 22 degrees C. to permit immunoreaction products to form. Thereafter the $^{125}$I-PMI-1/platelet immunoreaction products were isolated from the unbound $^{125}$I-PMI-1 by centrifugation of the entire maintained admixture through 0.3 ml of 20% sucrose in a Beckman Microfuge B (Beckman Instruments Inc., Fullerton, Calif.) to form a platelet pellet. The amount of radioactive $^{125}$I-PMI-1 associated with the platelet pellet was determined by scintillation spectrometry.

The results of this study, shown in FIG. 2, demonstrate that polypeptide p129–145 can competitively inhibit the binding of PMI-1 antibody molecules to platelet membrane-associated GPIIb in the absence of divalent cations. FIG. 2 indicates also that the approximate Kd of the p129–145/PMI-1 interaction is 1.2 uM because 50% inhibition was achieved at 1.6 uM polypeptide concentration when the antibody molecules were present at a concentration of 1 uM.

10. Expression of the hGPIIb Cryptic Determinant by Fibrinogen-Bound Platelets

Platelet rich plasma (PRP) was prepared as in Example 1a and divided into 3 aliquots. In one aliquot, the platelets were stimulated to express functional GPIIb-IIIa (fibrinogen receptors) by admixture of adenosine diphosphate (ADP) to a 50 uM final concentration to produce ADP-stimulated platelets. In the second aliquot, GPIIb-IIIa expression was stimulated by admixture of epinephrine to a 50 uM final concentration. In both cases, the GPIIb-IIIa fibrinogen receptors expressed on the stimulated platelets bound fibrinogen present in the plasma to produce fibrinogen-bound platelets. As a negative control, the third aliquot of PRP received no stimulus to produce non-stimulated platelets.

$^{125}$I-labeled PMI-1 Fab fragments, prepared by usual techniques from the $^{125}$I-labeled antibodies described in Example 6, were then admixed to a 0.8 uM final concentration with each of the PRP aliquots. The immunoreaction admixtures thus formed were maintained at 37 degrees C. for 30 minutes to permit formation of labeled immunoreaction products, i.e., fibrinogen-bound platelet/$^{125}$I-PMI-1 complexes. The label-containing immunoreaction products were then separated from unbound $^{125}$I-PMI-1 by centrifugation of the platelets through a sucrose cushion as described in Example 9B.

FIG. 3 illustrates the results of this study, and demonstrates that PMI-1 antibody molecules immunoreact with stimulated, fibrinogen-bound, platelets but do not substantially immunoreact with non-stimulated platelets. It is believed that the $^{125}$I-PMI-1 observed as "bound" in the non-stimulated PRP aliquot was due to non-specific binding ("sticking") and/or the presence of a naturally occurring background level of stimulated, fibrinogen-bound platelets or platelets stimulated and bound as a result of handling. These results therefore indicate that binding of fibrinogen, an arg-gly-asp (RGD) amino acid residue sequence-containing ligand, by the GPIIb-IIIa cytoadhesin results in expression of an otherwise cryptic antigenic determinant. Thus, PMI-1 antibody molecules, and antibody molecules of similar immunospecificity, can be used to assay for the presence and amount of stimulated, fibrinogen-bound platelets in a vascular fluid sample.

11. Inhibition of Platelet Aggregation by Polypeptides

Two hundred ul of the platelet rich plasma (PRP) prepared as described in Example 1A were admixed with 190 ul Tyrode's buffer containing BSA and dextrose (each at 1 mg/ml), and the various amounts of polypeptides p129-145 or p144-156 that are indicated in FIG. 4. Ten ul of ADP (80 uM in Tyrode's buffer) were then admixed to stimulate platelet aggregation. The admixture was maintained at 37 degrees C. while changes in light transmission of the admixture were monitored over time using a Dual Sample Aggregation Meter (Model DP-247E, Sienco Inc., Morrison, Colo.).

The aggregation meter was calibrated using a solution containing 200 ul PRP and 200 ul Tyrode's buffer to set a low baseline of light transmission at 5 percent for control aggregations and at 10 percent for aggregations in the presence of polypeptides. The upper limit of 100 percent light transmission was uniformly set using a mixture of 100 ml PRP and 300 ul Tyrode's buffer.

12. Immunoreaction of GPIIb Light Chain Using Anti-Peptide Antisera

About one billion platelets prepared as in Example 1A were resuspended in one ml of cold (i.e., 4 degrees C.) PBS and admixed with 200 ug of lactoperoxidase (Sigma) and 2 mCi of carrier-free Na$^{125}$I (16 mCi/ug, Amersham, Arlington Heights, Ill.) to form a platelet labeling suspension. Peroxide was then admixed with this suspension in two 5 ul additions from a 0.06% stock solution at 5 minute intervals and maintained throughout at 4 degrees C. to permit a labeling reaction to occur. Thereafter the reaction was stopped by admixing 200 ug of tyrosine and washed five items by repeated centrifugation at 1200 xg for 15 minutes followed by resuspension in cold PBS to form a labeled platelet suspension. After the fifth centrifugation step, the labeled platelets were lysed by resuspension in 40 ml lysis buffer (0.5% Triton X-100 [v/v], 10 mM EDTA, 10 ug/ml benzamidine and 100 units/ml Trasylol; all from Sigma) to form a labeled platelet lysate.

One ml of labeled platelet lysate was admixed with 15 ul of heat-inactivated normal rabbit serum (NRS) and maintained for 30 minutes at 22 degrees C., followed by further admixing 100 ul of a 10% (v/v) solution of Pansorbin (Behring Diagnostics, La Jolla, Calif.) prepared in immunoreaction buffer (IPB: 0.02M Tris-Cl, pH 7.4, 0,156M NaCl, 0.01M EDTA, 10 mM benzamidine-HCl, 10 ug/ml soybean trypsin inhibitor, 0.2 mM phenylmethylsulfonyl flouride, 1% [v/v] Triton X-100, 0.05% [v/v] Tween 20, 0.02% [w/v] NAN$_3$, 5 units/ml Trasylol; all from Sigma), centrifugation for 1 minute in a Beckman Microfuge B and isolation of the resulting supernatant to form a cleared lysate. This clearing procedure of admixing NRS, maintenance, admixing Pansorbin and centrifugation was repeated twice and then followed by the same procedure again using Pansorbin, but omitting the NRS and maintenance steps to form a thrice cleared lysate.

The thrice cleared lysate was then admixed with 250 ul of IPB, 4 ul of anti-polypeptide p144-156 antiserum prepared in Example 8, anti-GPIIb-IIIa prepared in Example 2 or NRS and bovine serum albumin (BSA) to a final concentration of 1% BSA in the resulting admixture. This resulting admixture was then maintained for 12-18 hours at 4 degrees C., further admixed with 100 ul of 10% Pansorbin and then maintained for 1 hour at 22 degrees C. Thereafter, the admixture was centrifuged in a Microfuge B for one minute and the resulting pellet was isolated. The isolated pellet was then washed twice in IPB, once in 0.5M LiCl and once again in IPB wherein washing includes resuspension in about 1 ml of the designated buffer followed by centrifugation for one minute in a Microfuge B and isolation of the resulting pellet.

The washed pellets were then solubilized to release any immune complexes present by heating for 3 minutes at 100 degrees C. in about 100 ml of the sample buffer described by Laemmli. See, for example, Laemmli, U.K., Nature (London), 227:680-685 (1970). Solubilized immune complexes were then centrifuged for one minute in a Microfuge B and the resulting supernatant containing immunoprecipitated proteins was analyzed by electrophoresis in a 15% polyacrylamide slab gel using Laemmli buffers containing 5% 2-mercaptoethanol. Thereafter the gels were dried and the proteins contained therein visualized by autoradiographic exposure to Kodak X-Omat AR film (Eastman Kodak, Rochester, N.Y.). Molecular weights of the resulting visualized proteins were estimated on the basis of electrophoretic mobility relative to $^{14}$C-labeled protein standards ranging between 12,300 and 97,400 daltons in molecular weight (New England Nuclear, Boston, Mass.).

Labeled lysates analyzed in this manner yielded a protein visualized on the resulting gels having a molecular weight of approximately 20 kDa, that corresponds to GPIIb light chain protein (1GPIIb), when anti-polypeptide p144-156 antiserum was used that was not substantially detected when polyclonal anti-GPIIb-IIIa antiserum or NRS was used. Therefore anti-polypeptide p144-156 antiserum, and antibody compositions of similar immunospecificity, can be used to detect 1GPIIb.

13. Expression of GPIIb-IIIa Cryptic Antigenic Determinants By Ligand Binding

A. Assay for Antibody Binding to Platelets That Express Cryptic Antigenic Determinants Washed platelets were prepared to a concentration of $1 \times 10^8$ per ml as described in Example 9A except that the Tyrode's buffer used was first treated by admixture with Chelex 100 (200–400 mesh sodium form, Bio-Rad Laboratories, Richmond, Calif.), maintained to complex any divalent cations present in the Tyrode's buffer and filtered to remove the complexed divalent cations from the buffer.

The above-prepared washed platelet-containing solution was divided into aliquots, and the platelets in each aliquot were then either stimulated by admixture with ADP to a 50 µM final concentration to form ADP-stimulated platelets or were not stimulated.

Monoclonal antibody compositions containing either $^{125}$I-labeled whole antibody molecules or $^{125}$I-labeled Fab fragments, prepared as described in Example 6, were admixed first with various polypeptides and either divalent cations or EDTA. The $^{125}$I-labeled antibody/peptide admixtures were then admixed with either stimulated or unstimulated platelet aliquots so that the antibody or Fab fragments were present at a concentration of about 0.8 uM. The resulting immunoreaction admixtures were then maintained for 30 min at 37 degrees C. to permit expression of the cryptic antigenic determinant and to permit the formation of $^{125}$I-labeled immunoreaction products, i.e., ligand-bound platelet/$^{125}$I-antibody or $^{125}$I-Fab fragment complexes. The label containing immunoreaction products were then separated from non-bound $^{125}$I-labeled antibody or Fab fragment by centrifugation of the platelet aliquot through a sucrose cushion as described in Example 9B.

Table 5 shows the results of assaying labeled-antibody binding to platelets in the presence of ligands using monoclonal antibody PMI-1.

TABLE 5

Ligand-Dependent Increase in PMI-1 IgG or Fab Binding to Platelets

| Antibody Species | Ligand[2] | Increase in PMI-1 Bound[1] | |
| --- | --- | --- | --- |
| | | Unstimulated | Stimulated |
| PMI-1 IgG | KYGRGDS | 6378 ± 753 | 6000 ± 714 |
| | GRGDSP | 5313 ± 522 | 5561 ± 158 |
| | GRGESP | 898 ± 357 | 837 ± 374 |
| | H-12 | N.D.[3] | 3663 ± 878 |
| | EDTA | 6064 ± 593 | 5674 ± 512 |
| PMI-1 Fab | KYGRGDS | 7722 ± 1189 | 5661 ± 373 |
| | GRGDSP | 4437 ± 852 | 5250 ± 300 |
| | GRGESP | −279 ± 281 | 147 ± 165 |
| | H-12 | N.D. | 3014 ± 430 |
| | EDTA | 5299 ± 225 | 6505 ± 560 |

[1]Increases in the amount of PMI-1 bound is expressed as molecules of PMI-1 bound per platelet ± one standard deviation observed where the increase is the amount bound in the presence of ligand less the amount bound in the absence of ligand but in the presence of 2 mM CaCl$_2$ and 1 mM MgCl$_2$. The amount bound in the presence of divalent cations but without ligand for unstimulated or stimulated platelets was 6769 ± 84 or 6643 ± 157 molecules/platelet for P MI-1 IgG respectively, and was 3917 ± 212 or 3785 ± 150 molecules/platelet for PMI-1 Fab.
[2]Ligand utilized was one of the indicated polypeptides, synthesized as described in Example 5 and added to a final concentration of 1 mM in the immunoreaction admixture described in Example 13A, or was the control polypeptide H-12, having the amino acid sequence HHLGGAKQAGDV and being derived from the fibrinogen gamma chain at residues 399–410, also at 1 mM, or was 4.5 mM EDTA added in the absence of ligand polypeptide as a control. In all cases where EDTA was not included, 2 mM CaCl$_2$ and 1 mM MgCl$_2$ were included.
[3]Not determined.

Table 6 shows the results of studying antibody binding to platelets in the presence of ligands using a monoclonal antibody composition containing whole antibody molecules or Fab fragments produced by hybridoma PMI-2 (i.e., a PMI-2 monoclonal antibody).

TABLE 6

| | | PMI-2 Bound[1] | |
| --- | --- | --- | --- |
| Ligand[2] | Divalent Ion[3] | Unstimulated | Stimulated |
| NONE | CaCl$_2$ | 1220 | 2,480 |
| RGDS | CaCl$_2$ | 2210 | 10,780 |
| SDGR | CaCl$_2$ | 1960 | 2,360 |
| GRGESP | CaCl$_2$ | 1560 | 4,680 |
| γ400–411 | CaCl$_2$ | 1840 | 9,650 |
| Fg | CaCl$_2$ | 2300 | 13,800 |
| NONE | EDTA | 8660 | 10,670 |
| RGDS | EDTA | 8540 | 10,080 |

[1]The amount of PMI-2 IgG bound was determined as described in Example 13A and is expressed as molecules of PMI-2 bound per platelet under the indicated immunoreaction conditions.
[2]Ligand utilized was one of the indicated polypeptides, prepared as described in Example 5 and added to a final concentration of 0.5 mM, or was a polypeptide having a sequence corresponding to the sequence of the fibrinogen gamma chain from residue position 400 to residue position 411 (γ40–411) also added to 0.5 mM, fibrinogen protein (Fg), isolated as described by Marguerie et al., J. Biol. Chem., 254:5357–5363 (1979) and utilized at a final concentration of 15 uM, or n o added ligand was utilized as a control.
[3]Divalent cation added was either 1 mM CaCl$_2$ or 5 mM EDTA.

The results shown in Tables 5 and 6 demonstrate the capacity of fibrinogen (Fg), the Fg-derived peptide, γ400–411, and RGD-containing peptides to bind GPIIb-IIIa and cause cryptic antigenic determinants recognized by either PMI-1 or PMI-2 to be exposed under conditions where these antigenic determinants are normally suppressed, namely in the presence of physiological concentrations of CaCl$_2$.

The results also demonstrate that the cryptic antigenic determinant recognized by PMI-2 is only inducible upon ligand binding with stimulated but not unstimulated platelets. In contrast, the cryptic antigenic determinant recognized by PMI-1 is inducible upon polypeptide ligand binding to both stimulated or nonstimulated platelets.

Further, the results also indicate the structural specificity of the ligand fop GPIIb-IIIa. A reverse peptide, SDGR, does not induce the PMI-2 recognized antigenic determinant, and a conservative substitution exchanging a glutamic acid (E) in place of the normally found aspartic acid residue (D) results in a peptide which is considerably less effective as a cryptic antigenic determinant inducing ligand.

When the concentration of the polypeptide ligand, RGDS, was varied in the above assay for antibody binding to platelets, a dose-response curve was generated for ligand induction of cryptic antigenic determinants present on either stimulated or unstimulated platelets. Results of the a dose-response curve are shown in FIG. 5, using either PMI-1 or PMI-2 IgG to detect the cryptic antigenic determinant, and are expressed as a percentage of LIBS induction. The amount of IgG bound in the presence of polypeptide was expressed as a percentage of the maximum amount of IgG bound upon complete ligand induced binding site (LIBS) induction, where IgG binding measured as molecules IgG per platelet in the presence of 4.5 mM EDTA, and in the absence of peptides, was considered to be 100% induction, and IgG binding, in the presence of 2 mM CaCl$_2$ and 1 mM MgCl$_2$ and in the absence of peptides, was considered to be 0% induction.

The results shown in FIG. 5 indicate that the polypeptide ligand induces two distinct cryptic antigenic determinants at similar half-maximal ligand concentrations of about 2 mM. In addition, the results show that whereas the determinant recognized by PMI-2 was inducible on stimulated platelets, but not on unstimulated platelets, the cryptic antigenic determinant recognized by PMI-1 was inducible on both stimulated and unstimulated platelets using the RGDS polypeptide.

It should be noted that while both PMI-1 and PMI-2 monoclonal antibodies are anti-LIBS monoclonal antibodies, the specificities of these two antibodies are distinguishable. Thus, occupancy of a receptor with a ligand can induce more than one LIBS. As a result, the methods of the present invention can be used to produce more than one distinct monoclonal antibody species that immunoreacts with a cell surface receptor-ligand complex.

B. Assay for Antibody. Binding to Soluble Purified GPIIb-IIIa That Expresses Cryptic Antigenic Determinants.

The ability of various polypeptide ligands to induce the expression of a cryptic antigenic determinant was studied using soluble isolated GPIIb-IIIa.

To that end, the competition ELISA was performed as described in Example 7B with the following exceptions. Microtiter plates were coated using a coating solution containing GPIIb-IIIa, isolated as described in Example 1, at a concentration of 10 μg per ml. After blocking, all solutions used were Chelex 100-treated before use, as described for Tyrode's buffer in Example 13A. Immunoreaction admixtures were prepared containing (1) 1.5 nanomolar PMI-1 IgG prepared as described in Example 5, or Tab hybridoma, as described in Example 7A, (2) 2 mM $CaCl_2$, (3) GPIIb-IIIa, isolated as described in Example 1, and added at a final concentration of 40 ug/ml for the PMI-1 assay and at 4 ug/ml for the Tab assay, and (4) polypeptide at 1 mM. The immunoreaction admixtures were maintained at 22 degrees C. for 16–20 hours to permit formation of a first solid phase-bound immunoreaction product between the solid phase-bound GPIIb-IIIa and admixed antibodies.

The results of the above studies are shown in Table 7 below.

TABLE 7

Expression of PMI-1 Defined Cryptic Antigenic Determinants Induced by Ligand Binding to GPIIb-IIIa in Solution

| Ligand[2] | Percent Expressed[1] | |
|---|---|---|
| | PMI-1 | Tab |
| KYGRGDS | 65 ± 22(3) | 98 ± 25(3) |
| GRGDSP | 53 ± 22(5) | 85 ± 27(3) |
| RGDS | 42 ± 16(3) | 92 ± 11(3) |
| GRGESP | 18 ± 13(3) | 106 ± 24(3) |
| SDGR | 18 ± 13(3) | 79 ± 25(3) |
| Control | 20 ± 9(5) | 84 ± 13(4) |

[1]The percent expressed is a measure of the cryptic antigenic determinant present on GPIIb-IIIa induced by polypeptide ligand binding. The data is presented as a percentage of the maximal determinant expression obtained using GPIIb-IIIa in the presence of 5 mM EDTA. The number of measurements that were made under each condition is indicated in the parenthesis and the results are the average ± the standard deviation of those measurements.
[2]The ligand added was a polypeptide, synthesized as described in Example 5, whose sequence is indicated by the single letter code shown. "Control" means that no polypeptide was added.

The results in Table 7 show that RGD-containing polypeptide ligands induce the expression of a cryptic antigenic determinant by GPIIb-IIIa in a manner analogous to that observed using intact platelets (see e.g., Table 6). The specificity of ligand induced expression was verified by using polypeptides having reversed sequences (SDGR) or conservative substitutions (GRGESP), and was further verified by observing no significant ligand influence upon Tab monoclonal antibody binding. These results indicate that ligand induced expression of the cryptic antigenic determinant recognized by monoclonal antibody PMI-1 is an intrinsic property of GPIIb-IIIa, and not dependent upon GPIIb-IIIa association with platelets.

The foregoing specification, including the specific embodiments need examples, is intended to be illustrative of the present invention and is not to be taken as limiting. Numerous other variations and modifications can be effected without departing from the true spirit and scope of the present invention.

What is claimed is:

1. A method of detecting in vivo the presence of a receptor-ligand complex wherein said complex contains a GPIIb-IIIa receptor and a ligand that are specifically bound, which comprises the steps of:

(a) intravenously administering to a human subject an effective amount of a monoclonal antibody composition comprising a physiologically tolerable diluent and antibody molecules that immunoreact with said GPIIb-IIIa receptor-ligand complex but do not immunoreact with the GPIIb-IIIa receptor or the ligand when either is in non-bound form, wherein said antibody molecules are linked to an in vivo indicating means;

(b) maintaining the administered subject for a predetermined time period sufficient for said antibody molecules to immunoreact with said receptor-ligand complex in vivo and form an immunoreaction product; and (c) assaying for the presence of any in vivo immunoreaction product formed in step b and thereby the presence of said complex in said subject.

2. The method of claim 1, wherein said antibody molecules are produced by hybridoma PMI-1 or PMI-2.

3. A method of inhibiting the aggregation of fibrinogen-bound platelets, which method comprises the steps of:

(a) admixing platelets with an effective amount of a physiologically tolerable diluent comprising a hGPIIb cryptic determinant polypeptide analog that is capable of inhibiting the aggregation of fibrinogen-bound platelets; and (b) maintaining said admixture for a predetermined time period sufficient for said polypeptide analog to inhibit the aggregation of fibrinogen-bound platelets, wherein said hGPIIb cryptic determinant polypeptide analog corresponds to the sequence represented by the formula PSPSPIHPAHHKRDRRQ.

4. A method of inhibiting the aggregation of fibrinogen-bound platelets in vivo, which method comprises the steps of:

(a) intravenously administering to a human subject an effective amount of a pharmaceutically acceptable composition consisting essentially of antibody molecules produced by hybridoma PMI-1 that immunoreact with stimulated, fibrinogen-bound platelets; and (b) maintaining the administered subject for a predetermined time period sufficient for said composition to inhibit the aggregation of fibrinogen-bound platelets.

* * * * *